United States Patent
Gu et al.

(10) Patent No.: US 11,896,673 B2
(45) Date of Patent: *Feb. 13, 2024

(54) GLUCOSE RESPONSIVE INSULIN DELIVERY COMPOSITIONS AND METHODS

(71) Applicant: NORTH CAROLINA STATE UNIVERSITY, Raleigh, NC (US)

(72) Inventors: Zhen Gu, Raleigh, NC (US); Chao Wang, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 306 days.

This patent is subject to a terminal disclaimer.

(21) Appl. No.: 17/188,583

(22) Filed: Mar. 1, 2021

(65) Prior Publication Data
US 2021/0260198 A1 Aug. 26, 2021

Related U.S. Application Data

(63) Continuation of application No. 16/070,223, filed as application No. PCT/US2017/013793 on Jan. 17, 2017, now Pat. No. 10,946,102.

(60) Provisional application No. 62/278,614, filed on Jan. 14, 2016.

(51) Int. Cl.
| | |
|---|---|
| A61K 38/28 | (2006.01) |
| A61K 47/54 | (2017.01) |
| A61K 47/69 | (2017.01) |
| C07H 13/08 | (2006.01) |
| A61K 47/60 | (2017.01) |
| A61K 47/64 | (2017.01) |
| A61P 3/10 | (2006.01) |
| A61K 9/00 | (2006.01) |
| A61K 35/18 | (2015.01) |

(52) U.S. Cl.
CPC .......... *A61K 47/549* (2017.08); *A61K 9/0021* (2013.01); *A61K 35/18* (2013.01); *A61K 38/28* (2013.01); *A61K 47/60* (2017.08); *A61K 47/64* (2017.08); *A61K 47/6937* (2017.08); *A61P 3/10* (2018.01); *C07H 13/08* (2013.01)

(58) Field of Classification Search
CPC .......... A61K 47/549; A61K 38/28; A61P 3/10; A61P 47/60
See application file for complete search history.

(56) References Cited

U.S. PATENT DOCUMENTS

| | | | |
|---|---|---|---|
| 9,585,934 B2 * | 3/2017 | Soliman | A61K 38/10 |
| 2014/0037699 A1 | 2/2014 | Zion et al. | |
| 2014/0275476 A1 | 9/2014 | Lancaster et al. | |
| 2014/0356384 A1 | 12/2014 | Hubbell et al. | |
| 2015/0105317 A1 | 4/2015 | Lin et al. | |
| 2015/0320837 A1 | 11/2015 | Anderson et al. | |
| 2015/0353639 A1 | 12/2015 | Watts et al. | |

FOREIGN PATENT DOCUMENTS

| | | |
|---|---|---|
| CN | 103568160 | 2/2014 |
| CN | 103705494 | 4/2014 |
| CN | 104271148 | 1/2015 |
| CN | 104520325 | 4/2015 |
| WO | 2014183071 | 11/2014 |

OTHER PUBLICATIONS

English Translation of Second Office Action for Chinese Application No. 2017800166598 dated Sep. 30, 2021, 11 pages.
International Search Report, dated Mar. 31, 2017, in connection with International Patent Application No. PCT/US2017/013793.
International Preliminary Report on Patentability issued for International Application No. PCT/US2017/013793, dated Jul. 26, 2018.
Adams, et al., Diabetes Mellitus and Closed-Loop Insulin Delivery. Biotechnology and Genetic Engineering Reviews, 455-496 (2013).
Anselmo, A. C. et al. Delivering nanoparticles to lungs while avoiding liver and spleen through adsorption on red blood cells. ACS Nano 7, 11129-11137 (2013).
Association, A. D. Standards of medical care in diabetes—2014. Diabetes Care 37, S14 (2014).
Bariya, S. H., Gohel, M. C., Mehta, T. A. & Sharma, O. P. Microneedles: an emerging transdermal drug delivery system. Journal of Pharmacy and Pharmacology 64, 11-29 (2012).
Brownlee, M. & Cerami, A. A glucose-controlled insulin-delivery system: semisynthetic insulin bound to lectin. Science 206, 1190-1191 (1979).
Chou, D. H.-C et al. Glucose-responsive insulin activity by covalent modification with aliphatic phenylboronic acid conjugates. Proc. Natl. Acad. Sci. U.S.A. 112, 2401-2406 (2015).
Deng, D. et al. Crystal structure of the human glucose transporter GLUT1. Nature 510, 121-125 (2014).
Glycated Insulin. Accessed on-line https://www.rndsystems.com/resources/articles/glycated-insulin (2015), 3 pages.
Gu, Z. et al. Glucose-responsive microgels integrated with enzyme nanocapsules for closed-loop insulin delivery. ACS Nano 7, 6758-6766 (2013).

(Continued)

*Primary Examiner* — Gyan Chandra
(74) *Attorney, Agent, or Firm* — Meunier Carlin & Curfman LLC

(57) ABSTRACT

Disclosed herein is a glucose-responsive insulin delivery system based on the interaction between the glucose-modified insulin and glucose transporters (GLUTs) on erythrocytes (or red blood cells, RBCs). After being conjugated with glucose, insulin can efficiently bind to RBC membranes. The binding is reversible in the setting of hyperglycemia, resulting in fast release of insulin and subsequent drop of blood glucose (BG) level in vivo. In some embodiments, the delivery vehicle can include: 1) intravenously injectable polymeric nanoparticles (~100 nm in diameter) coated with RBC membrane and loaded with glucose-modified insulin and/or 2) painless microneedle (MN) patches loaded with the complex of GLUT and glucose-modified insulin.

20 Claims, 36 Drawing Sheets

(56) References Cited

OTHER PUBLICATIONS

Gu, Z. et al. Injectable nano-network for glucose-mediated insulin delivery. ACS Nano 7, 4194-4201 (2013).

Hu, C.-M. J. et al. Erythrocyte membrane-camouflaged polymeric nanoparticles as a biomimetic delivery platform. Proc. Natl. Acad. Sci. U.S.A. 108, 10980-10985 (2011).

Kataoka, K., Miyazaki, H., Bunya, M., Okano, T. & Sakurai, Y. Totally synthetic polymer gels responding to external glucose concentration: their preparation and application to on-off regulation of insulin release. J. Am. Chem. Soc. 120, 12694-12695 (1998).

Kim, H., Kang, Y. J., Kang, S. & Kim, K. T. Monosaccharide-responsive release of insulin from polymersomes of polyboroxole block copolymers at neutral pH. J. Am. Chem. Soc. 134, 4030-4033 (2012).

Kowalski, A. Pathway to artificial pancreas systems revisited: moving downstream. Diabetes Care 38, 1036-1043 (2015).

Like, A. A. & Rossini, A. A. Streptozotocin-induced pancreatic insulitis: new model of diabetes mellitus. Science 193, 415-417 (1976).

Martanto, W. et al. Transdermal delivery of insulin using microneedles in vivo. Pharmaceutical research 21, 947-952 (2004) doi:Doi 10.1023/B:Pham.0000029282.44140.2e.

Mayes, et al., Sugar Binding Polymers Showing High Anomeric and Epimeric Discrimination Obtained by Noncovalent Molecular Imprinting. Analytical Biochemistry vol. 222, Issue 2, 483-488, (1994).

Mi, F.-L. et al. Oral delivery of peptide drugs using nanoparticles self-assembled by poly (γ-glutamic acid) and a chitosan derivative functionalized by trimethylation. Bioconjugate Chem. 19, 1248-1255 (2008).

Mo, R., Jiang, T., Di, J., Tai, W. & Gu, Z. Emerging micro-and nanotechnology based synthetic approaches for insulin delivery. Chem. Soc. Rev. 43, 3595-3629 (2014).

Montel-Hagen, A. et al. The Glut1 and Glut4 glucose transporters are differentially expressed during perinatal and postnatal erythropoiesis. Blood 112, 4729-4738 (2008).

Montel-Hagen, A., Sitbon, M. & Taylor, N. Erythroid glucose transporters. Curr Opin Hematol. 16, 165-172 (2009).

Mueckler, M. & Thorens, B. The SLC2 (GLUT) family of membrane transporters. Mol. Aspects Med. 34, 121-138 (2013).

Mueckler, M. Facilitative glucose transporters. Eur. J. Biochem. 219, 713-725 (1994).

Mukthavaram, R., Shi, G., Kesari, S. & Simberg, D. Targeting and depletion of circulating leukocytes and cancer cells by lipophilic antibody-modified erythrocytes. J. Controlled Release 183, 146-153 (2014).

Mura, S., Nicolas, J. & Couvreur, P. Stimuli-responsive nanocarriers for drug delivery. Nat. Mater. 12, 991-1003 (2013).

Muzykantov, V. R. Drug delivery by red blood cells: vascular carriers designed by mother nature. Expert Opin. Drug Deliv. 7, 403-427 (2010).

Pickup, J. & Keen, H. Continuous Subcutaneous Insulin Infusion at 25 Years Evidence base for the expanding use of insulin pump therapy in type 1 diabetes. Diabetes Care 25, 593-598 (2002).

Podual, K., Doyle, F. J. & Peppas, N. A. Glucose-sensitivity of glucose oxidase-containing cationic copolymer hydrogels having poly (ethylene glycol) grafts. J. Control Release 67, 9-17 (2000).

Prausnitz, M. R. & Langer, R. Transdermal drug delivery. Nature biotechnology 26, 1261-1268 (2008).

Prausnitz, M. R., Mitragotri, S. & Langer, R. Current status and future potential of transdermal drug delivery. Nature Reviews Drug Discovery 3, 115-124 (2004).

Raskin, P. et al. Initiating Insulin Therapy in Type 2 Diabetes A comparison of biphasic and basal insulin analogs. Diabetes Care 28, 260-265 (2005).

Shaw, J. E., Sicree, R. A. & Zimmet, P. Z. Global estimates of the prevalence of diabetes for 2010 and 2030. Diabetes Res. Clin. Pr. 87, 4-14 (2010).

Shemin, D. & Rittenberg, D. The life span of the human red blood cell. J. Biol. Chem. 166, 627-636 (1946).

Song, et al., Glycation and Insulin Resistance—Novel Mechanisms and Unique Targets? Arterioscler Thromb Vasc Biol. 32, 1760-1765, (2012).

Sun, L. et al. Crystal structure of a bacterial homologue of glucose transporters GLUT1-4. Nature 490, 361-366 (2012).

Sun, X., Wang, C., Gao, M., Hu, A. & Liu, Z. Remotely Controlled Red Blood Cell Carriers for Cancer Targeting and Near-Infrared Light-Triggered Drug Release in Combined Photothermal-Chemotherapy. Adv. Funct. Mater. 25, 2386-2394 (2015).

Tai, W. et al. Bio-inspired synthetic nanovesicles for glucose-responsive release of insulin. Biomacromolecules 15, 3495-3502 (2014).

Veiseh, O., Tang, B. C., Whitehead, K. A., Anderson, D. G. & Langer, R. Managing diabetes with nanomedicine: challenges and opportunities. Nat. Rev. Drug Discov. 14, 45-57 (2015).

Villa, C. H. et al. Delivery of drugs bound to erythrocytes: new avenues for an old intravascular carrier. Ther. Deliv. 6, 795-826 (2015).

Vrhovac, I., Breljak, D. & Sabolić, I. Glucose transporters in the mammalian blood cells. Period. Biol. 116, 131-138 (2014).

Wang, C. et al. Multifunctional Theranostic Red Blood Cells for Magnetic-Field-Enhanced in vivo Combination Therapy of Cancer. Adv. Mater. 26, 4794-4802 (2014).

Wu, Q., Wang, L., Yu, H., Wang, J. & Chen, Z. Organization of glucose-responsive systems and their properties. Chem. Rev. 111, 7855-7875 (2011).

Wu, W., Mitra, N., Yan, E. C. & Zhou, S. Multifunctional hybrid nanogel for integration of optical glucose sensing and self-regulated insulin release at physiological pH. ACS nano 4, 4831-4839 (2010).

Wu, Z. et al. Turning erythrocytes into functional micromotors. ACS Nano 8, 12041-12048 (2014).

Yu, J. et al. Microneedle-array patches loaded with hypoxia-sensitive vesicles provide fast glucose-responsive insulin delivery. Proc. Natl. Acad. Sci. U.S.A. 112, 8260-8265 (2015).

Office Action issued for Chinese Application No. 201780016659.8, dated Apr. 19, 2021.

Che-Ming J. Hu et al., "Erythrocyte Membrane-camouflaged Polymeric Nanoparticles as a Biomimetic Delivery Platform", PNAS, 2011, 108(27), 10981.

Wang, Chao, et al. "Red blood cells for glucose-responsive insulin delivery." Advanced Materials 29.18 (2017): 1606617.

* cited by examiner

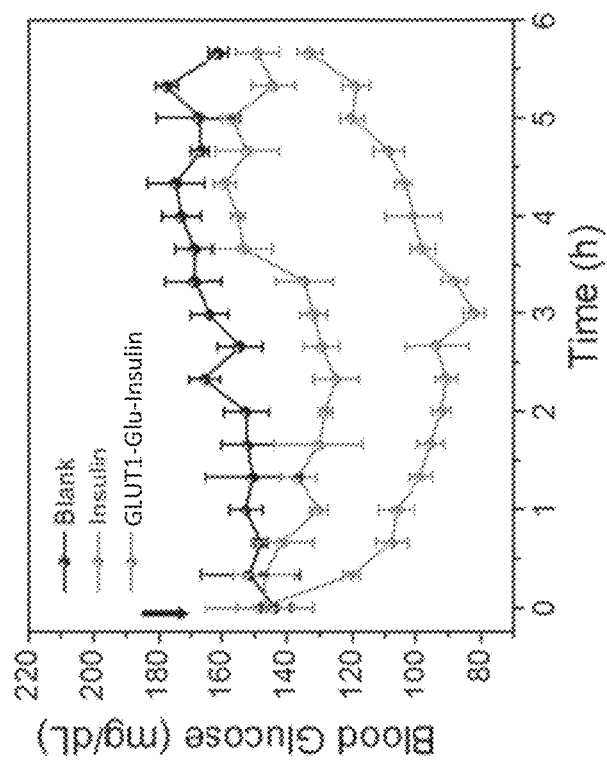
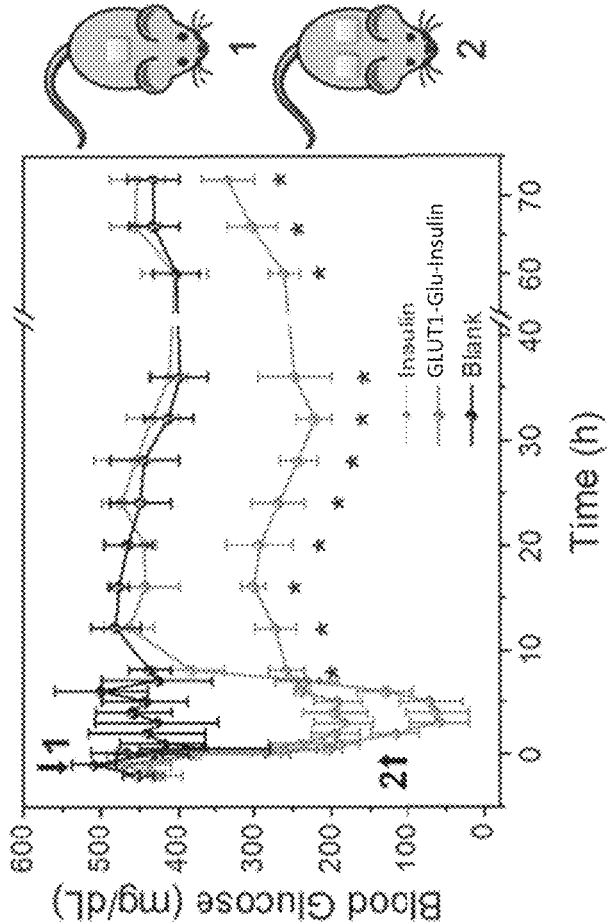
FIG. 18G
FIG. 18H

GLUCOSE RESPONSIVE INSULIN DELIVERY COMPOSITIONS AND METHODS

CROSS-REFERENCE TO RELATED APPLICATIONS

This application is a continuation of U.S. patent application Ser. No. 16/070,223, filed Jul. 13, 2018, which is a national phase application, filed pursuant to 35 U.S.C. § 371, of International Application No. PCT/US2017/013793, filed Jan. 17, 2017, which claims benefit of U.S. Provisional Application No. 62/278,614, filed Jan. 14, 2016. Each of the aforementioned applications is hereby incorporated herein by reference in its entirety.

STATEMENT REGARDING FEDERALLY SPONSORED RESEARCH OR DEVELOPMENT

This invention was made with Government Support under Grant No. 1UL1TR001111 awarded by the National Institutes of Health. The Government has certain rights in the invention.

BACKGROUND

Diabetes currently affects 415 million people worldwide and this number is expected to increase to 642 million by 2040. Insulin is essential for survival in type 1 diabetes and often required for treatment of type 2 diabetes in order to control glycemia and prevent complications. However, traditional exogenous insulin administration cannot match the exquisite regulation of blood glucose achieved by β-cells within the pancreatic islets of Langerhans, where endogenous insulin secretion is linked through metabolism to glucose transport. Poor glucose control results in a high risk for diabetes complications, such as limb amputation, blindness and kidney failure. In addition, hypoglycemia can lead to behavioral and cognitive disturbance, seizure, coma, brain damage, or death. "Smart" glucose-responsive insulin delivery devices or formulations, which can mimic the function of β-cells to regulate insulin "secretion," are therefore highly desirable with an aim to improve blood glucose control and quality of life for people with diabetes.

Such "smart" therapies generally integrate a glucose-sensing or conversion module and a sensing/conversion-activated insulin releasing module. For example, the wearable closed-loop electronic/mechanical pumps combine a continuous glucose-monitoring electrochemical sensor and an external insulin infusion pump. These systems have historically been limited by lag in blood glucose equilibration with the interstium, insulin absorption into the circulation and biofouling. Synthetic materials-based glucose-responsive formulations have also been widely explored since the 1970's. Three classical strategies are often utilized, typically including different glucose-sensing moieties: glucose oxidase, glucose binding proteins (GPB) (e.g., ConA) (14) and phenylboronic acid (PBA) for achieving glucose triggers. A variety of formulations, such as bulk hydrogels, microgels, emulsion-based nanoparticles and self-assembled vesicles have been developed to respond toward a hyperglycemic state to swell, shrink, degrade, or dissociate in order to promote the release of insulin. In spite of these promising strategies, it remains challenging to demonstrate a system that responds rapidly to elevated blood glucose (BG) levels, closely mirroring the kinetics of a healthy pancreas. In addition, immunological responses, stability in the physiological environment and long-term toxicity of those synthetic systems require further investigation.

SUMMARY

Disclosed herein are glucose-responsive insulin delivery compositions that can be used to control glucose levels in a subject. In particular, a composition is disclosed that comprises a glucose-modified insulin molecule that comprises an insulin moiety conjugated to at least one glucose moiety, e.g. by at least one linker molecule. In these embodiments, the glucose-modified insulin molecule is configured to reversibly bind a glucose binding structure such that the glucose-modified insulin is displaced by endogenous glucose in high glucose conditions. This results in the bioavailability of the glucose-modified insulin molecule where it can promote glucose metabolism. Since the rate of release is dependent on glucose concentration, glucose levels can be tightly regulated.

In some embodiments, the glucose-modified insulin molecule comprises 2, 3, 4, 5, 6, or more glucose moieties conjugated to the insulin moiety by a distinct linker molecule. For example, the linker molecule can be synthetic. In some embodiments, the linker molecule comprises a maleimide group. In some embodiments, the linker molecule comprises a polyethylene glycol (PEG) group. In some cases, the linker molecule is a peptide linker, such as a peptide having 1, 2, 3, 4, 5, 6, 7, 8, 9, 10, or more amino acids.

The insulin moiety can any bioactive form of insulin, such as human insulin or an insulin homologue. The insulin is preferably a recombinant protein. The insulin can be rapid-acting (e.g. lispro, aspart, glulisine), short-acting (regular insulin, velosulin, novolin), intermediate-acting (NPH), or long-acting (insulin glargine, insulin detemir, insulin degludec). In some embodiments, the disclosed composition comprises a mixture of glucose-modified insulin molecules having different forms of insulin moieties.

In some cases, the user mixes the composition comprising the glucose-modified insulin molecule with a glucose binding structure prior to administration to a subject under conditions suitable for the glucose-modified insulin molecule to reversibly bind the glucose binding structure. In other embodiments, the composition comprises glucose-modified insulin molecule already bound to the glucose binding structure.

The glucose binding structure can be any biocompatible substrate capable of reversibly binding glucose in vivo. For example, the structure can comprises a glucose transporter (GLUT) protein, which is a membrane protein that facilitates the transport of glucose over a plasma membrane. GLUT1 is a glucose transporter that is expressed at highest levels in red blood cells (erythrocytes). Therefore, in particular embodiments, the glucose-binding structure is a red blood cell (erythrocyte), such as a human red blood cell. However, in other embodiments, the glucose-binding structure comprises only the plasma membrane of an erythrocyte, or other cell that comprises a GLUT protein. For example, the plasma membrane can be attached to a biocompatible nanoparticle. Suitable nanoparticles can in some embodiments have a mean diameter of about 50 to about 150 nanometers, including about 50, 60, 70, 80, 90, 100, 110, 120, 130, 140, and 150 nanometers. In some embodiments, the nanoparticle comprises Poly(Lactide-co-Glycolide) (PLGA) copolymer. In some embodiments, the nanoparticle is formed from dextran. In some embodiments, the nanoparticle is formed from hyaluronic acid. In some embodiments, the nanoparticle is a liposome.

The glucose-modified insulin molecule is configured to be displaced from the glucose-binding structure in high glucose conditions. In some embodiments, the glucose-modified insulin molecule is configured to be displaced from the glucose-binding structure when glucose levels reach or exceed about 200 mg/dL. While it is understood that the glucose-modified insulin molecule can still be displaced from the glucose-binding structure at low glucose levels, it will do so at a much lower rate. Therefore, in some embodiments, the glucose-binding structure preferentially binds the glucose-modified insulin in a physiological, low glucose environment, e.g. glucose concentrations from 0 to 200 mg/dL. In preferred embodiments, the glucose-binding structure is configured to stably bind the glucose-modified insulin in these low glucose conditions for at least 10, 20, 30, 40, or 50 days. In some embodiments, these kinetics can be tuned through the linker property between hormone and the glucose-derivative.

Also disclosed is a method of controlling insulin levels in a subject using the disclosed glucose-responsive insulin delivery compositions. In particular, the disclosed method can involve administering a therapeutically effective amount of the disclosed composition to a subject diagnosed with diabetes. In some embodiments, the subject has type I diabetes. In some embodiments, the subject has type II diabetes. In some embodiments, the subject has gestational diabetes. The disclosed methods can in some cases be used instead of an insulin pump. In addition, the disclosed method can in some cases allow for a reduction in the need and/or frequency of glucose monitoring.

The disclosed composition can be administered in any manner suitable for exposure to glucose in the circulation. In some embodiments, the composition is delivered by a transdermal patch. For example, the composition can be delivered by a microneedle-array patch.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 18A-H shows data and images from in vivo studies of the MN-array patches for type 1 diabetes treatment. FIG. 18A is a photograph of the smart insulin patch with an MN array. FIG. 18B is a SEM image of MN array (Scale bar: 200 micrometers). FIG. 18C is a fluorescence microscopy image of MN-loaded GULT1-Insulin with FITC labeled insulin (Scale bar: 200 micrometers). FIG. 18D is a graph showing the in vivo blood glucose (BG) levels in STZ-induced diabetic mice after treatment with blank MNs, free insulin loaded MNs and GLUT1-Insulin loaded MNs. The black arrows indicate the administration points. FIG. 18E is a graph showing the results of an in vivo glucose tolerance test toward diabetic mice, with the GLUT1-Insulin MNs injected at time 0 and an IPGTT performed 1.5 hours following insulin administration. The black arrows indicate the administration points. FIG. 18F shows the change in plasma insulin levels and glucose levels after IPGTT. FIG. 18G is a graph showing the BG levels of diabetic mice treated with additional administration of the MN-array patch 1 hour post administration of GLUT1-Insulin MNs. FIG. 18H is a graph showing the BG changes of healthy mice administered by blank MNs, free insulin loaded MNs and GLUT1-Insulin loaded MNs over time. The error bars are based on the standard deviation (SD) of five mice per group. (P values: *P<0.05)

DETAILED DESCRIPTION

Figure 1A:
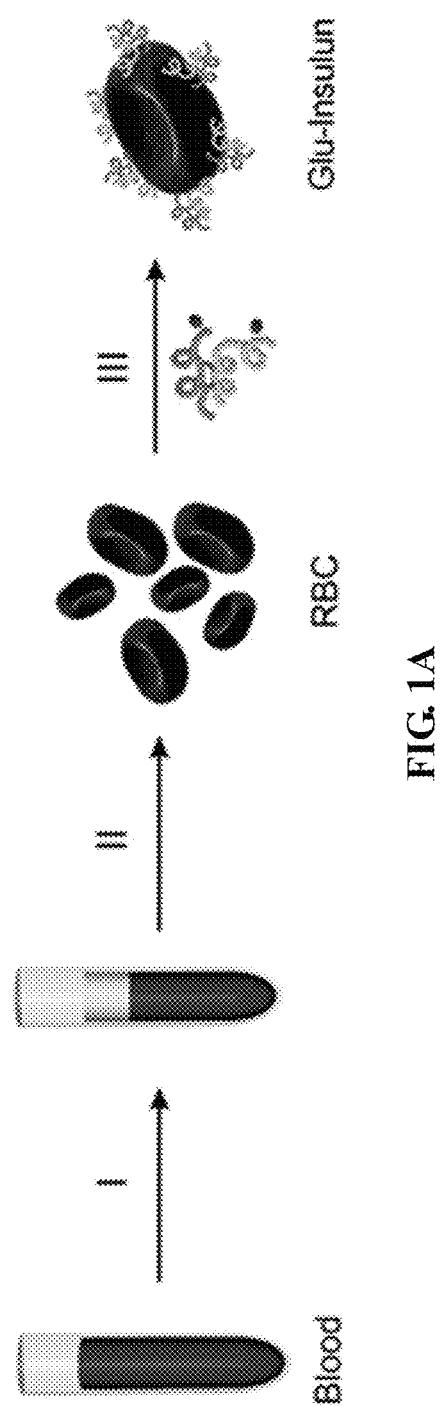
FIG. 1A shows a schematic of the glucose-responsive insulin delivery system based on red blood cells. Synthesized Glu-Insulin was attached to red blood cells (erythrocytes) by interacting with glucose receptor/transporter on plasma membranes. I and II, collection and isolation of mRBCs. III, binding of Glu-Insulin to mRBCs.
Figure 1B:
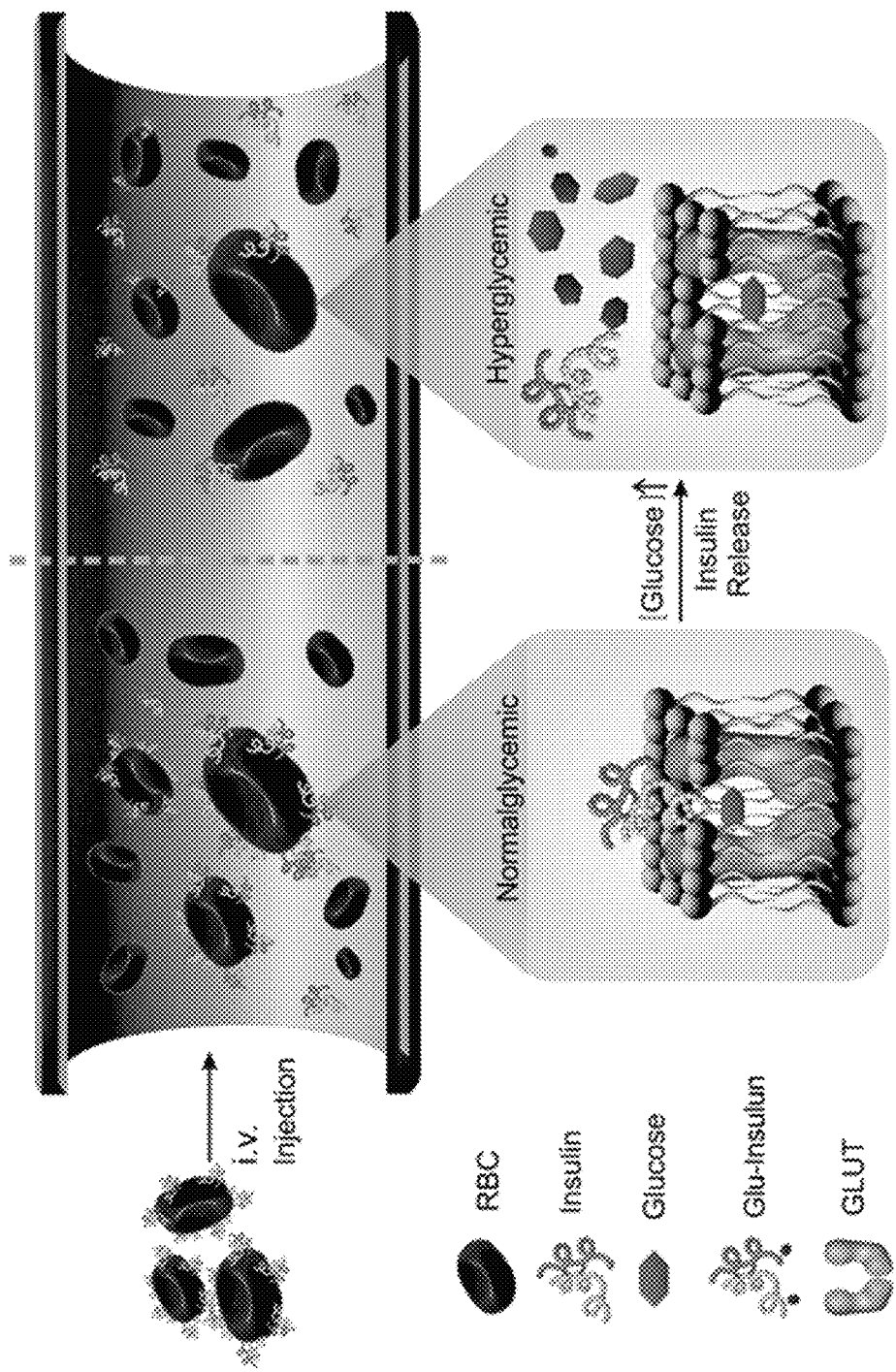
FIG. 1B shows a schematic of insulin-attached red blood cells for in vivo insulin delivery triggered by a hyperglycemic state to release more insulin.

Disclosed herein is a composition and method for treating diabetes. The composition includes a glucose-modified insulin molecule that includes an insulin moiety conjugated to at least one glucose moiety. The insulin and glucose moieties of the glucose-modified insulin molecule are conjugated by at least one linker molecule. In some embodiments, the composition further includes at least one glucose-binding structure. The glucose binding structure is configured to reversibly bind the glucose moiety of the glucose-modified insulin molecule, releasing the glucose-modified insulin in high glucose conditions. The method of treating diabetes includes administering the composition including the glucose-modified insulin molecule and the glucose-binding structure to a subject, wherein the glucose-modified insulin molecule is bound to the glucose-binding structure. In some embodiments, a pharmaceutically effective amount of the composition is administered to a subject having diabetes.

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Activities" of a protein, including those relating to "bioactivity," include, for example, transcription, translation, intracellular translocation, secretion, phosphorylation by kinases, cleavage by proteases, and/or homophilic and heterophilic binding to other proteins.

The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. Administering can be performed using transdermal microneedle-array patches. The term "parenteral" includes subcutaneous, intravenous, intramuscular, intra-articular, intra-synovial, intrasternal, intrathecal, intrahepatic, intralesional, and intracranial injections or infusion techniques.

"Biocompatible" generally refers to a material and any metabolites or degradation products thereof that are generally non-toxic to the recipient and do not cause any significant adverse effects to the subject.

A "composition" is intended to include a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

As used herein, "conjugated" refers to a non-reversible binding interaction.

As used herein, "displace" refers to interrupting a molecular or chemical interaction between, for example, a protein domain and a peptide, a protein domain and a chemical, a protein domain and a nucleic acid sequence by a chemical, peptide, or nucleic acid having affinity for that specific protein domain than the peptide, chemical, or nucleic acid being displaced.

An "effective amount" is an amount sufficient to effect beneficial or desired results. An effective amount can be administered in one or more administrations, applications or dosages.

As used herein, the term "high glucose conditions" refers to an environment having a glucose concentration greater than or equal to 200 mg/dL. For example, "high blood glucose levels" refer to glucose levels in the blood stream greater than or equal to 200 mg/dL. In some embodiments, high glucose conditions are 200-400 mg/dL. In other embodiments, high glucose conditions are 300-400 mg/dL.

A "linker" as used herein refers to a molecule that joins adjacent molecules. Generally a linker has no specific biological activity other than to join the adjacent molecules or to preserve some minimum distance or other spatial relationship between them. In some cases, the linker can be selected to influence or stabilize some property of the adjacent molecules, such as the folding, net charge, or hydrophobicity of the molecule.

As used herein, the term "low glucose conditions" refers to an environment having a glucose concentration from 0 to 200 mg/dL. For example, "low blood glucose levels" refer to glucose levels in the blood stream less than 200 mg/dL.

The terms "peptide," "protein," and "polypeptide" are used interchangeably to refer to a natural or synthetic molecule comprising two or more amino acids linked by the carboxyl group of one amino acid to the alpha amino group of another.

The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

A "primer" is a short polynucleotide, generally with a free 3-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in "PCR: A PRACTICAL APPROACH" (M. MacPherson et al., IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "therapeutically effective amount" or "therapeutically effective dose" refer to the amount of a composition, such as glucose-modified insulin bound to a glucose-binding structure, that will elicit the biological or medical response of a tissue, system, animal, or human that is being sought by the researcher, veterinarian, medical doctor or other clinician over a generalized period of time. In some embodiments, a desired response is the control of type I diabetes. In some embodiments, a desired response is the control of type II diabetes. In some instances, a desired biological or medical response is achieved following administration of multiple dosages of the composition to the subject over a period of days, weeks, or years.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

"Transformation" of a cellular organism with DNA means introducing DNA into an organism so that at least a portion of the DNA is replicable, either as an extrachromosomal element or by chromosomal integration. "Transfection" of a cellular organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of *E. coli*. Typical eukaryotic host cells are mammalian, such as Chinese hamster ovary or cells of human origin. The introduced DNA sequence may be from the same species as the host cell of a different species from the host cell, or it may be a hybrid DNA sequence, containing some foreign and some homologous DNA.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection.

In some instances, the terms "treat", "treating," "treatment" and grammatical variations thereof, include controlling blood sugar levels and reducing the severity of diabetes symptoms as compared with prior to treatment of the subject or as compared with the incidence of such symptom in a general or study population.

The term "specifically binds," as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

Disclosed herein is a composition and method for treating diabetes. The composition includes a glucose-modified insulin molecule that includes an insulin moiety conjugated to at least one glucose moiety. The insulin and glucose moieties of the glucose-modified insulin molecule are conjugated by at least one linker molecule. The glucose-modified insulin molecule is configured to reversibly bind a glucose-binding structure, releasing the glucose-modified insulin in high glucose conditions. In some embodiments, the composition further includes at least one glucose-binding structure. The method of treating diabetes includes providing a composition including the glucose-modified insulin molecule and the glucose-binding structure, wherein the glucose-modified insulin molecule is bound to the glucose-binding structure. The method further includes administering a therapeutically effective amount of the composition to a subject having diabetes.

The invention includes a composition for glucose-responsive insulin delivery based on the reversible interaction between glucose-modified insulin (Glu-Insulin) and a glucose-binding structure. Such binding is reversible and insulin can be released from RBCs under high glucose conditions. A potential mechanism for this release is the displacement of the Glu-Insulin due to competitive interaction of free glucose with GLUT. Human RBCs have a life span of 100-120 days as natural carriers for oxygen in the blood vessels. Therefore, these inherently biocompatible natural carriers could prolong the circulation of medicine in blood. (21-27) In the following examples, intravenous (i.v.) injection of mouse RBCs (mRBCs) coupled with Glu-Insulin is shown to prolong the therapeutic effect of insulin to maintain blood glucose (BG) levels within the normal range compared with free insulin in chemically induced type I mice. In vivo glucose-responsive behavior was observed through a glucose tolerance test. Alternate strategies of administration include 1) i.v. injectable polymeric nanoparticles (approximately 100 nm in diameter) coated with RBC membrane and loaded with glucose-modified insulin and 2)

a microneedle (MN)[35-58] patch platform loaded with the complex of exogenously expressed GLUTs and Glu-insulin.

In some implementations, the glucose-modified insulin molecule can comprise two or more glucose moieties. In some implementations, the glucose-modified insulin molecule comprises two glucose moieties. In some implementations, each glucose moiety is conjugated to the insulin moiety by a distinct linker molecule. The linker molecule can be any natural or synthetic molecule that serves to attach the glucose moiety to the insulin moiety. In some examples, the linker molecule includes a maleimide group, or a maleimide-thiol adduct. In a particular example, a maleimide group is added to a glucose molecule, and a thiol group is added to an insulin molecule. The maleimide-glucose and thiolated insulin are then reacted to form the glucose-modified insulin molecule, wherein the maleimide-thiol adduct acts as a linker molecule. Alternatively or in addition, the linker molecule can include a spacer. The spacer may be a polymer chain, such as a poly(ethylene glycol) (PEG) chain or a chain of any other suitable polymer.

The glucose-modified insulin molecule is configured to reversibly bind a glucose binding structure. The reversible binding can be achieved by non-covalent binding between the glucose and one or more glucose binding moieties. In some implementations, the glucose binding moiety is a glucose binding protein. Accordingly, in some implementations, the glucose binding structure can be any structure comprising one or more glucose binding proteins. In some implementations, the glucose binding structure can be a single glucose binding protein. In some implementations, the glucose binding proteins are glucose transporter proteins, and the non-covalent binding is a receptor-ligand binding interaction. Non-limiting examples of glucose binding proteins are all members of the GLUT or SLC2A families, including GLUT1, GLUT2, GLUT3, GLUT4, GLUT5, GLUT6, GLUT7, GLUT8, GLUT9, GLUT10, GLUT11, GLUT12, and SLC2A13.

The glucose-binding structure comprising one or more glucose binding moieties includes, but is not limited to, structures such as a cell, a cell membrane, a nanoparticle and a microparticle. Accordingly, in some implementations, the glucose-binding structure is a cell. The cell may be any cell type, human, mammalian. In some examples, the cells used as glucose-binding structures are human red blood cells. Advantageously, autologously derived cells may be drawn from a subject, exposed to the glucose-modified insulin in low-glucose (binding) conditions, and then delivered back to the same subject. However, the cells need not be autologously derived for the composition to serve the function of releasing bound glucose-modified insulin under high glucose conditions.

In other implementations, the glucose-binding structure is a red blood cell membrane attached to a nanoparticle or a microparticle. The nanoparticle can have any appropriate measurement. For example, nanoparticle sizes can range from 5 to 500 nanometers in diameter. In some implementations, nanoparticle sizes measure between 50-150 nanometers in diameter. The nanoparticle can also be of any appropriate material or substance, and in some implementations, is a poly lactic-co-glycolic acid (PLGA) nanoparticle. For example, PLGA nanoparticles (NPs) can be coated with RBC membranes (RM-PLGA) using similar methods as those described below. As with intact mRBCs, Glu-Insulin can likewise bind to RM-PLGA NPs specifically and insulin release from these nanoparticles is self-regulated in a BG-mediated manner. Compared with mRBCs, human RBCs (hRBCs) showed better performance for insulin loading and glucose-responsive release in the described system, possibly due to the greater density and affinity of the facilitative glucose transporters on hRBCs than mRBCs (28). Other nanomaterials or nanoparticles may be used as an alternative or in addition to PLGA. Other possible nanomaterials or nanoparticles can include polymeric materials (for example, dextran or hyaluronic acid), liposomes, and/or inorganic nanoparticles.

The glucose-modified insulin is configured to release the glucose-binding structure in high glucose conditions. This facilitates the release of a portion of the glucose-modified insulin when, for example, blood glucose levels rise above a certain threshold. For example, under high glucose conditions, anywhere from 10%-95% of the glucose-modified insulin molecule may be released from the glucose-binding structure, including 10%, 15%, 20%, 25%, 30%, 35%, 40%, 45%, 50%, 55%, 60%, 65%, 70%, 75%, 80%, 85%, 90%, or 95% of the glucose-modified insulin. As used herein, high glucose conditions are considered to be greater than or equal to 200 mg/dL. In some embodiments, high glucose conditions are 200-400 mg/dL. In other embodiments, high glucose conditions are 300-400 mg/dL. Low glucose conditions are considered to be less than 200 mg/dL.

In some implementations, under low glucose conditions, the glucose-binding structure is configured to bind the glucose-modified insulin for at least 50 days. In some implementations, the glucose-binding structure may bind the glucose-modified insulin for even greater time periods if the glucose conditions remain low. For example, red blood cells have a lifespan of 100-120 days. Glucose-modified insulin carried by red blood cells may remain bound for the duration of the lifespan of the cell carrier in low glucose conditions.

Also disclosed herein are methods of using the glucose-modified insulin compositions to treat diabetes. The method of treating diabetes includes first administering a composition such as any of those described above. In some implementations, a therapeutically effective amount of glucose-modified insulin molecule bound to a glucose-binding structure is administered to a subject having or suspected of having diabetes. In some implementations, the therapeutically effective amount of glucose-modified insulin molecule bound to a glucose-binding structure can be administered via a transdermal patch, such as a microneedle-array patch. The method can also include, in some implementations, exposing the glucose-modified insulin to a glucose-binding moiety or to a glucose-binding structure such as a red blood cell, nanoparticle, or microparticle. Advantageously, autologously derived cells, such as red blood cells, may be drawn from a subject, exposed to the glucose-modified insulin in low-glucose (binding) conditions, and then delivered back to the same subject. However, the cells need not be autologously derived for the composition to serve the function of releasing bound glucose-modified insulin under high glucose conditions.

It is challenging to demonstrate a combination of fast response, long-term persistence and biocompatibility in glucose-responsive insulin delivery formulations. The glucose-modified insulin strategies described herein present effective approaches. In some examples, these strategies can be extended to personalized cell therapy, and/or integrated with a variety of therapeutics for treating different diseases with merits of both long-term sustained release and physiological signal-mediated controlled release.

EXAMPLES

Methods Used in Examples 1-4

Materials. All chemicals were purchased from Sigma-Aldrich unless otherwise specified and were used as received. Human recombinant insulin (Zn salt, 27.5 IU/mg) was purchased from Life Technology.

Synthesis of Glu-Insulin. Glu-Insulin conjugate was synthesized by a two-step process. In brief, insulin (or insulin-FITC) was thiolated by reacting with the Traut's Reagent (2-iminothiolane, Pierce) in PBS (pH=8.0) at a molar ratio of 1:5 for 2 h at 4° C. After 2 h of reaction, excess Traut's Reagent was removed using a centrifugal filter device (molecular weight cut-off MWCO=3 kDa) to purify the SH-insulin. In the meantime, D-(+)-Glucosamine was mixed with sulfosuccinimidyl-4-(N-maleimidomethyl)-cyclohexane-1-carboxylate (Sulfo-SMCC, Pierce) in PBS (pH=7.4) at a molar ratio of 1:1 for 2 h at RT. At last, the SMCC activated glucose and insulin-SH was mixed in PBS (pH=8.0) at a molar ratio of insulin:glucose=1:100. After 24 h reaction at 4° C., excess glucose was removed using the centrifugal filter device (MWCO=3 kDa). The obtained Glu-Insulin was stored at 4° C. until use.

Preparation of insulin loaded RBCs. Whole blood was collected from the B16 mice or from a human volunteer (The study protocol was approved by the Institutional Review Board at North Carolina State University). RBCs were separated from the whole blood by centrifugation (1000 g, 10 min) and washed thrice with cold PBS (300 mOsm, pH=8.0) to remove the glucose intracellularly. To load the insulin to RBC membrane, Glu-Insulin (0.5 mg/ml) was incubated with 500p RBCs ($1\times10^8$) under gentle stirring at 4° C. overnight. RBCs were washed thrice with cold PBS (300 mOsm, pH 8) to remove the unconjugated Glu-Insulin. Bound insulin was determined by ELISA assay.

Preparation of insulin—PLGA-RM nanoparticles. PLGA polymer was dissolved in acetone 15 mg mL$^{-1}$. 1 mL PLGA solution was added to 4 mL ddH$_2$O in a glass vial, and the glass vial was kept under vacuum overnight to remove acetone and obtain PLGA-NPs in water. To coat with RBC membrane, RBCs were resuspended in 0.2 mM EDTA water solution to induce membrane rupture 10 min and then adjusted to PBS. The cell solution was centrifuged at 10000 g for 10 min. The cell membrane was washed several times until supernatant was free of red color. PLGA-NPs were mixed with the vesicle solution to obtain a final PLGA-RM nanoparticles ratio of 75 mL blood per mg of PLGA-NPs. To load the insulin to PLGA-RM, Glu-Insulin was incubated with PLGA-RM NPs under gentle stirring at 4° C. overnight. PLGA-RM NPs were washed thrice by centrifugation with cold PBS (pH 8) to remove the unconjugated Glu-Insulin. The obtained insulin–PLGA-RM nanoparticles were stored at 4° C. until use (loading capacity: 2%).

Preparation of GLUT1-Glu-insulin conjugates. The gene encoding GLUT1 was amplified from the plasmid prGT3 (Addgene 15993) and sub-cloned into pET-28a vector (Novagen) with primers GLUT1-s (5'-GCAAATGGGTCGCGGATCCATGGAGCCCAGCAGC-3', SEQ ID NO:1) and rGLUT-a (5'-CGAGTGCGGCCGCAAGCTTTCACACTTGGGAGTC AG-3', SEQ ID NO:2). The obtained pET28a-GLUT1 was transformed into *E. coli* Rosetta (DE3) pLysS cells for GLUT1 expression. Briefly, a fresh *E. coli* colony was inoculated into 5 mL LB medium (supplemented with 10 μg/mL kanamycin and 34 μg/mL chloromycetin). After culture at 37° C. overnight, the cell culture was then diluted with fresh LB medium by 100-fold and continued to culture for another 2-3 hours (OD600 0.6-0.8). Afterwards, 0.5 mM isopropyl β-D-1-thiogalactopy-ranoside (IPTG) was added to induce GLUT1 expression at 20° C. for 8 hours. The cells were collected by centrifugation at 4000×g for 15 minutes and resuspended in Buffer A (20 mM Tris-HCl pH 8.0, 0.15 M NaCl, 10 mM imidazole, 5% glycerol, 1 mM PMSF, 0.5 mg/mL lysozyme, 0.4 mg/mL DNase I and 2% DDM). The suspension was incubated at room temperature for 30 minutes and on ice for another 30 minutes. The cells were then lysed by sonication and cell debris was removed by centrifugation (20000×g, 10 minutes). The clear lysate was added to a column containing 1 mL Ni-NTA resin (Qiagen). After washing the column with Buffer B (20 mM Tris-HCl pH 8.0, 0.15 M NaCl, 25 mM imidazole, 5% glycerol and 0.05% DDM), GLUT1 was eluted with Buffer C (20 mM Tris-HCl pH 8.0, 0.15 M NaCl and 500 mM imidazole, 5% glycerol and 0.05% DDM). The purified GLUT1 was quantified by Bradford assay (Bio-Rad) and analyzed by SDS-PAGE.

Glucose modified insulin was mixed with GLUT1 protein at a molar ratio of 1.2:1 for 12 hours at 4° C. Free Glu-insulin were removed by the centrifugal filter device (MWCO=10 kDa). The obtained Glu-Insulin was stored at 4° C. until use. We first examined the specific binding affinity of free GLUT1 proteins and Glu-Insulin in vitro. We incubated the GLUT1 with Glu-Insulin overnight, free Glu-Insulin was removed by centrifugal filter device (MWCO=10 kDa). It was clearly found that insulin signals could be detected in supernatant if co-incubated with GLUT1 proteins.

Western blot. The total proteins of PLGA-RM were collected by centrifugation for 10 min at 10000 rpm. Afterwards, 30 μg of total protein was separated on 12% sodium dodecyl sulfate (SDS) Bis-Tris-Polyacrylamide gels and then electrically transferred (at 250 mA for 75 min) onto nitrocellulose membranes (BioRad, 0.45 μm). After that, the membranes were blocked in TBST (BioRad) containing 3% bovine serum albumin (BSA) for 1 h at room temperature, and then incubated in TBST containing 3% BSA and primary antibody against GLUT4 (1:500, Thermo Scientific, USA) overnight at 4° C. After being incubated with primary antibody, membranes were washed thrice with TBST and incubated with goat anti-rabbit IgG-HRP secondary antibody (1:5000, Thermo Scientific, USA) for 1 h at room temperature. Finally, membranes were stained by 1-Step™ TMB-Blotting Substrate Solution (Thermo Scientific) after thrice washing with TBST.

Synthesis and characterization of acrylate modified HA (m-HA). 1.0 g of HA was dissolved in 50 mL of DI water at 4° C., to which 0.8 mL of methacrylic anhydride (MA) was added dropwise. The reaction solution was adjusted to pH 8-9 by the addition of 5N NaOH and stirred at 4° C. for 24 hours. The resulting polymer was obtained by precipitation in acetone, followed by washing with ethanol several times. The product was re-dissolved in DI water and the solution dialyzed against DI water for two days. m-HA was achieved by lyophilization with a yield of 87.5%. The degree of modification was calculated to be 15% by comparing the ratio of the areas under the proton peaks at 5.74 and 6.17 ppm (methacrylate protons) to the peak at 1.99 ppm (N-acetyl glucosamine of HA) after performing a standard deconvolution algorithm to separate closely spaced peaks.

m-HA: 1H NMR (D2O, 300 MHz, δ ppm): 1.85-1.96 (m, 3H, CH2=C(CH3)CO), 1.99 (s, 3H, NHCOCH3), 5.74 (s, 1H, CH1H2=C(CH3)CO), 6.17 (s, 1H, CH1H2=C(CH3) CO).

In Vitro Release Studies. After preparation of the insulin-RBCs or insulin–PLGA-RM NPs, various solutions (0, 100, 200 or 400 mg dL$^{-1}$ glucose in 500 μL PBS) were added to each tube and incubated at 37° C. to evaluate the release of insulin. After washing with PBS three times by centrifugation, the released insulin in supernatant was determined by ELISA assay. (Calbiotech, USA). For insulin release from GLUT1-Insulin conjugates, the GLUT1-Insulin conjugates treated with various solutions (0, 100, 200 or 400 mg dL$^{-1}$ glucose in 500 µL PBS), the released insulin was separated using the centrifugal filter device (MWCO=10 kDa). The released insulin in centrifugal tube was determined by ELISA assay. (Calbiotech, USA).

Fabrication and characterization of MNs. All of the MNs in this study were fabricated using six uniform silicone molds from Blueacre Technology Ltd. machined by directly laser ablation to create arrays of cylindrical holes. Each MN had a 300 µm by 300 µm round base tapering to a height of 600 µm with a tip radius of around 5 µm. The MNs were arranged in a 15 by 15 array with 600 µm tip-to-tip spacing. After preparation of the GLUT1-Insulin conjugates, total prepared GLUT1-Insulin (1 mg/kg) was dispersed in 3 mL premixed m-HA (w/v=40%) with N,N'-methylenebisacrylamide (MBA, w/v=20%) and photo initiator (Irgacure 2959, w/v=0.05%) in a bath sonicator for several minutes. The solution was added to the prepared micromold reservoir. After that, the micromolds were transferred to a Hettich Universal 32R centrifuge for 20 min at 2000 rpm to compact solution into MN cavities. The final device underwent 6-8 hours drying at 25° C. in a vacuum dessicator. After desiccation was completed, the MN arrays were carefully separated from the silicone mold and was exposed to UV light (wavelength: 320-450 nm) for 30 seconds. The needle base can be tailored to fit the injection syringe. The resulting product can be stored in a sealed six well container for up to 30 days at 4° C. The fluorescent MNs were fabricated with nanoparticle made from FITC labeled insulin. The morphology of the MNs was characterized on a FEI Verios 460L field-emission scanning electron microscope (FESEM). The fluorescence image of MNs were taken by Olympus IX70 multi-parameter fluorescence microscope. The UV cross-linking process was conducted using Dymax BlueWave 75 UV Curing Spot Lamp.

Mechanical strength test. The mechanical strength measurements of MNs have been conducted under ambient and isometric test conditions on a tensile load frame. The tensile force was continuously monitored as a stainless steel plate compressing arrays of MNs along the y-direction on a stress-strain gauge. The initial gauge was set as 2.00 mm between the MNs tips and the stainless steel plate, 10.00 N as load cell capacity. The speed of the top stainless steel plate movement towards the MN-array patch was 0.1 mm/second. The failure force of MNs was recorded as the needle began to buckle.

Skin penetration efficiency test. The MN-arrays were applied to the dorsum of mouse skin for 30 minutes and removed. The mice were euthanized and the skin samples were embedded in OCT compound (Sakura Finetek) and flash-frozen in an isopentane bath on dry ice. The frozen tissues were sectioned (10-µm thickness), mounted on microscope slides, and stored at -80° C. The samples were hematoxylin and eosin (H&E) stained in the Histology Laboratory at NC State College of Veterinary Medicine. In a separate experiment, the surface sites of excited skin were stained by trypan blue for 5 min. After wiping off residual dye from the skin surface with dry tissue paper, the skin sample was imaged by optical microscopy (Leica EZ4 D stereo microscope).

In Vivo Studies Using STZ-Induced Diabetic Mice. STZ-induced male C57B6 diabetic mice were purchased from Jackson Labs (USA) and used under protocols approved by the Institutional Animal Care and Use Committee at North Carolina State University. For in vivo circulating behavior of insulin-RBC, mRBCs were coupled with FITC after loading with insulin, 3 mice were injected i.v. with autologous insulin-mRBCs. Then ~3 µL of blood was extracted from the tail vein at different time points and then dispersed in 0.5 mL of PBS with anticoagulants. Flow cytometry measurement was applied to determine the percentages of insulin-mRBCs (positive in FITC) in the blood samples. For diabetes treatment effect using insulin-RBC or insulin–PLGA-RM nanoparticles, five mice for each group were selected for intravenous injection with 200 µL PBS, free insulin, RBC/insulin, or insulin loaded mRBCs, or insulin–PLGA-RM nanoparticles, with an insulin dose of 1 mg/kg for each mouse. For diabetes treatment using MN-array patches, five mice for each group were selected for transcutaneous treatment with blank MNs, MNs loaded with insulin or MNs loaded with GLUT1-insulin conjugates, with an insulin dose of 1 mg/kg for each mouse. Skin adhesive was used to immobilize the MNs patch to the back of mice. The BG level was measured from tail vein blood samples (approximately 3 µL) of mice using the Clarity GL2Plus glucose meter (Clarity Diagnostics) at different time points. To measure in vivo insulin concentration, plasma was collected from mice at different time points and was stored frozen at -80° C. until assayed. Plasma insulin concentrations were determined using the human insulin ELISA kit (Calbiotech, USA).

Statistical analysis. Statistical analysis was evaluated using GraphPad Prism (5.0). Statistical significances were calculated with the paired Student t test and two-way ANOVA. P values of 0.05 or less were considered significant.

Example 1. Synthesis and Characterization of Glucose-Modified Insulin (Glu-Insulin)

Figure 2:
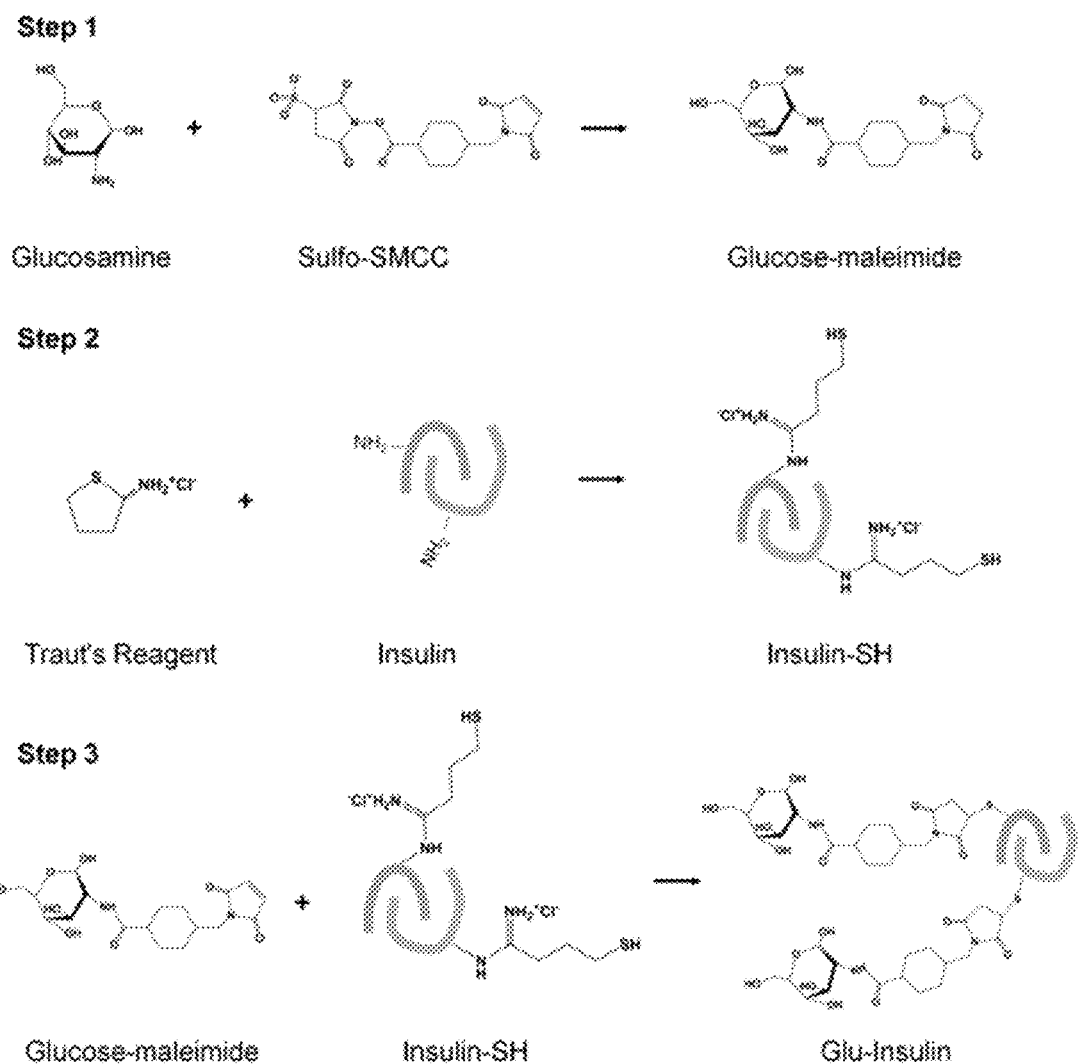
FIG. 2 shows the synthesis steps of conjugating glucose to insulin.
Figure 3A:
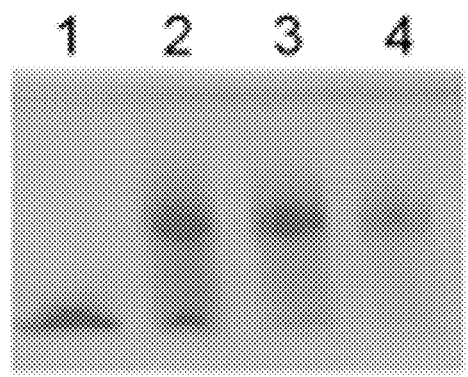
FIG. 3A shows sodium dodecyl sulfate polyacrylamide gel electrophoresis (SDS-PAGE) of glucose-insulin conjugates. The molar ratio of glucose to insulin was (1) 0:1, (2) 1:1, (3) 10:1 and (4) 100:1. When conjugated with glucose, the molecular weight of insulin increased so that they could be distinguished with native insulin in SDS-PAGE. In addition, the products obtained were mainly glucose-insulin conjugates when the ratio of glucose to insulin increased to 100:1.
Figure 3B:
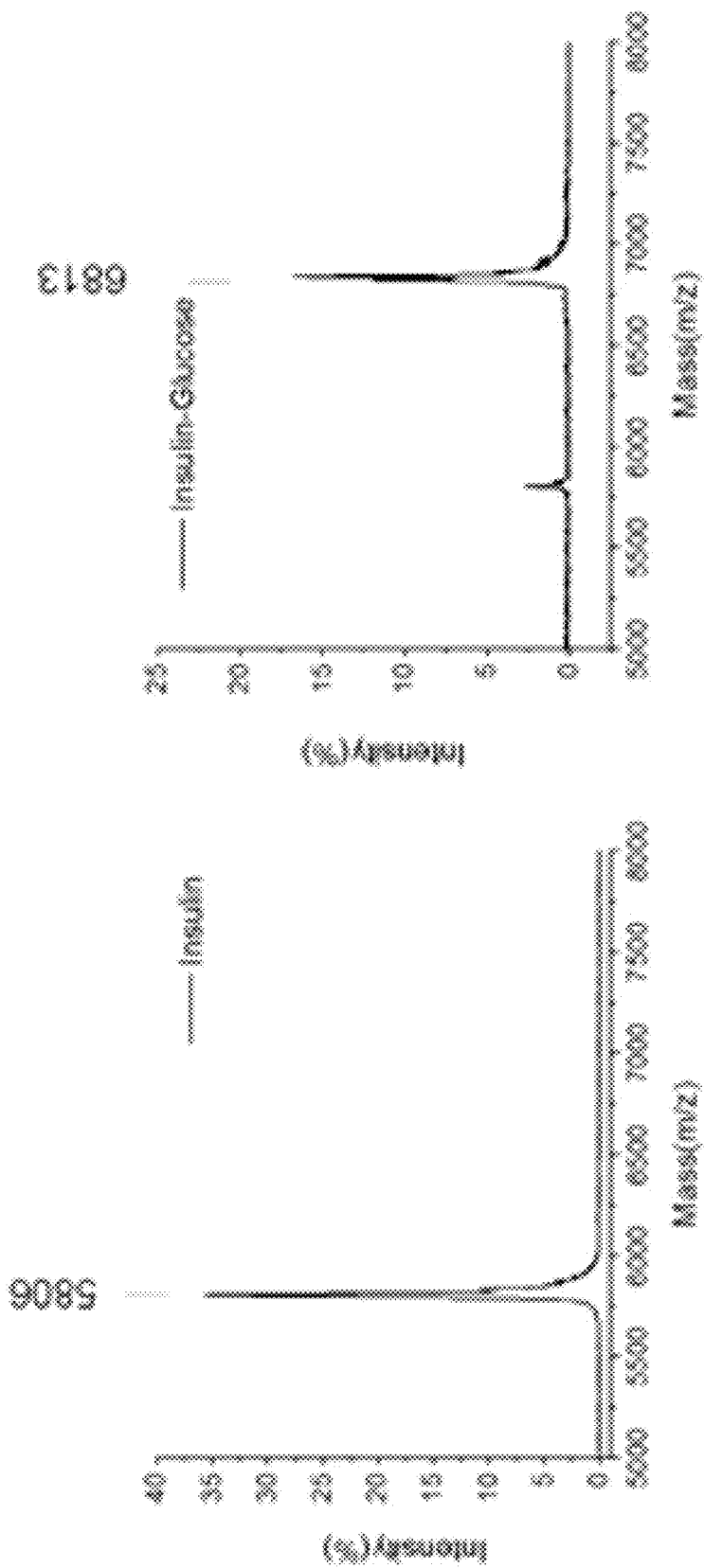
FIG. 3B shows the results of a matrix-assisted laser desorption/ionization mass spectrometry (MALDI MS) assay of native insulin and glucose-insulin conjugates. The molecular weight of native insulin was approximately 5806 and glucose-insulin conjugates was approximately 6813.
Figure 4A:
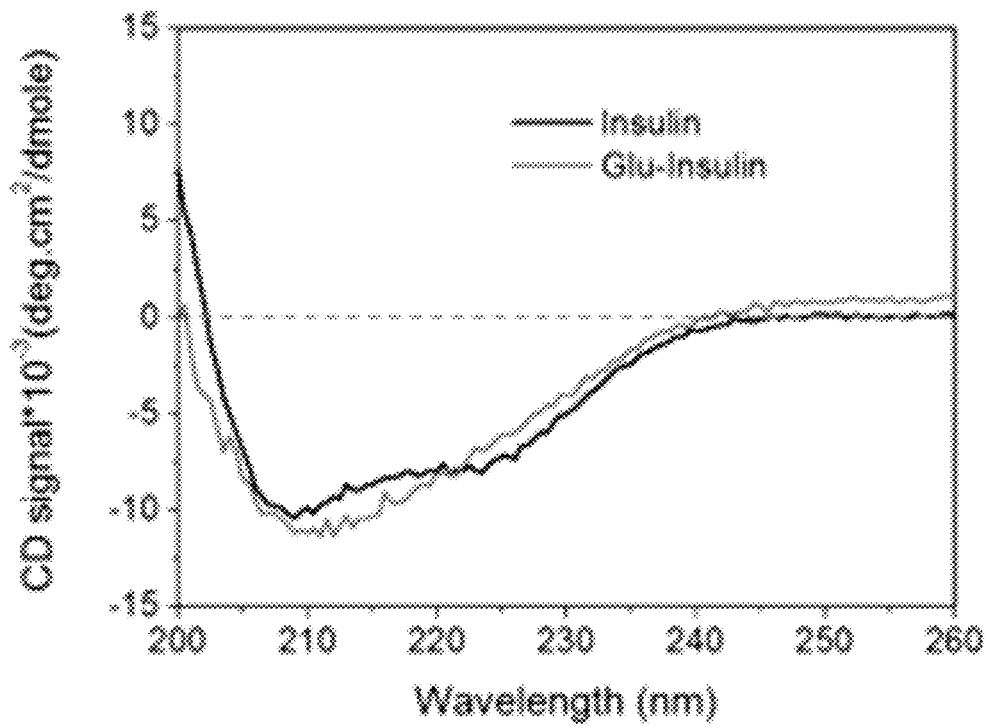
FIG. 4A shows a CD spectra of native insulin and glucose-insulin conjugates.
Figure 4B:
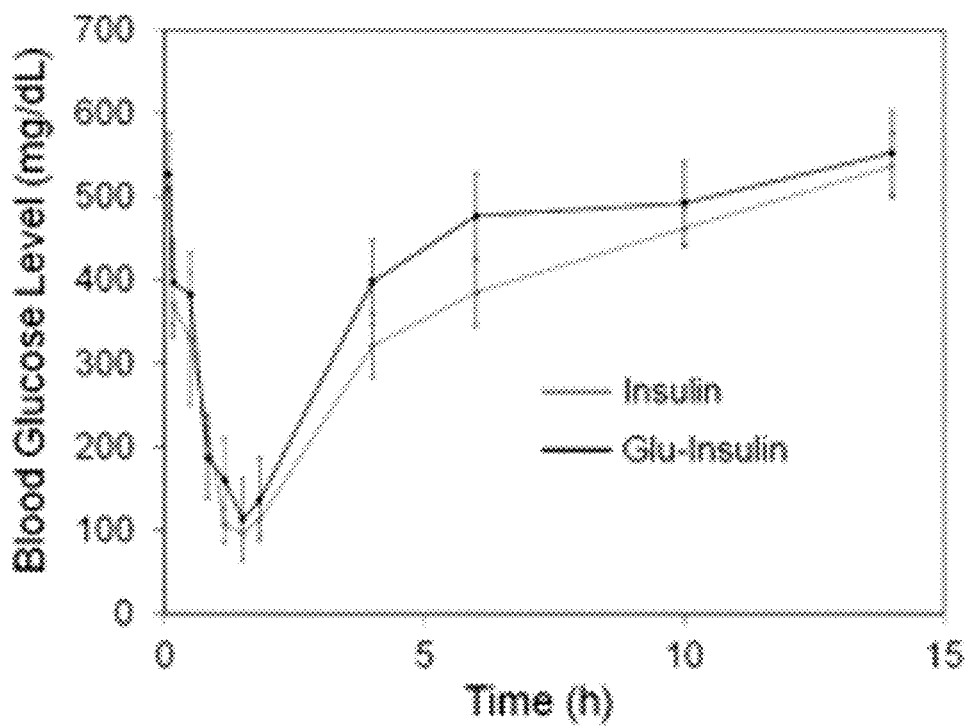
FIG. 4B shows the results of an in vivo bioactivity comparison of the native insulin and glucose-insulin conjugates in STZ-induced type 1 diabetic mice with the same insulin concentration (5 mg/kg).

Glucose was conjugated to insulin via a bifunctional maleimide linker (FIG. 2). Glu-Insulin was clearly identified by the sodium dodecyl sulfate polyacrylamide gel electrophoresis (SDS-PAGE) and matrix-assisted laser desorption/ionization mass spectrometry (MALDI MS) (FIG. 3A-B). As calculated by MALDI-MS, two glucose molecules are conjugated to each insulin molecule (feed molar ratio of glucose to insulin: 100:1). The circular dichroism (CD) spectra of native insulin and Glu-Insulin are virtually superimposable, indicating that the secondary structures of these species are similar if not substantially identical (FIG. 4A). Most importantly, the Glu-Insulin conjugate and native insulin do not display any significant difference in their bioactivity profiles upon administration in streptozotocin (STZ)-induced type 1 diabetic mice (FIG. 4B). In short, the modification of insulin with glucose has a statistically insignificant impact on bioactivity relative to unmodified insulin.

Figure 5A:
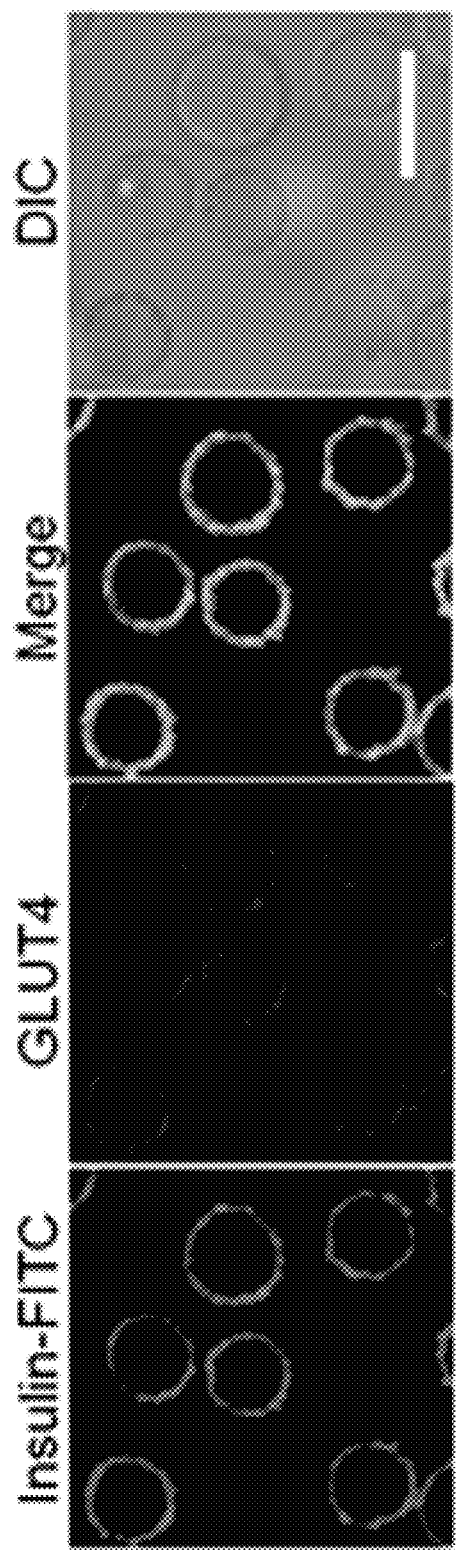
FIG. 5A shows confocal microscopy images of the Glu-insulin attached to mRBCs. (Scale bar=10 μm).
Figure 5B:
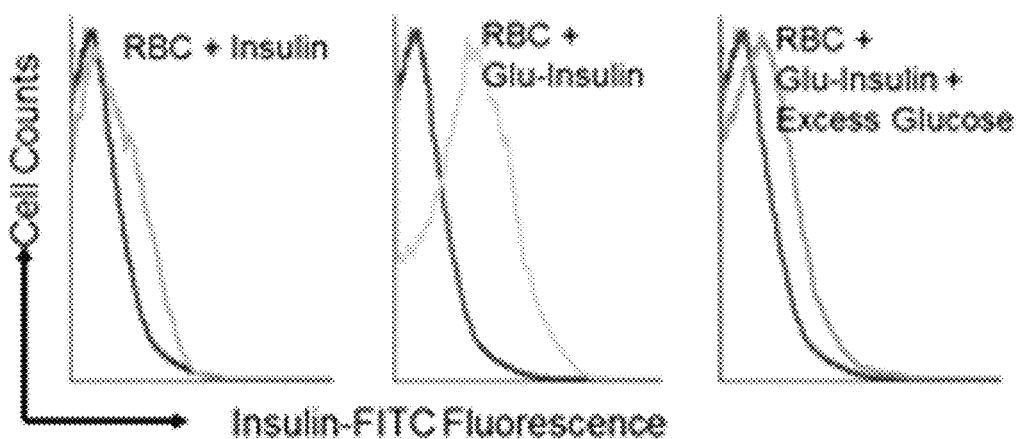
FIG. 5B shows flow cytometry data of mRBCs incubated with different experimental settings showing the successful binding of the insulin on the cell membrane.
Figure 6A:
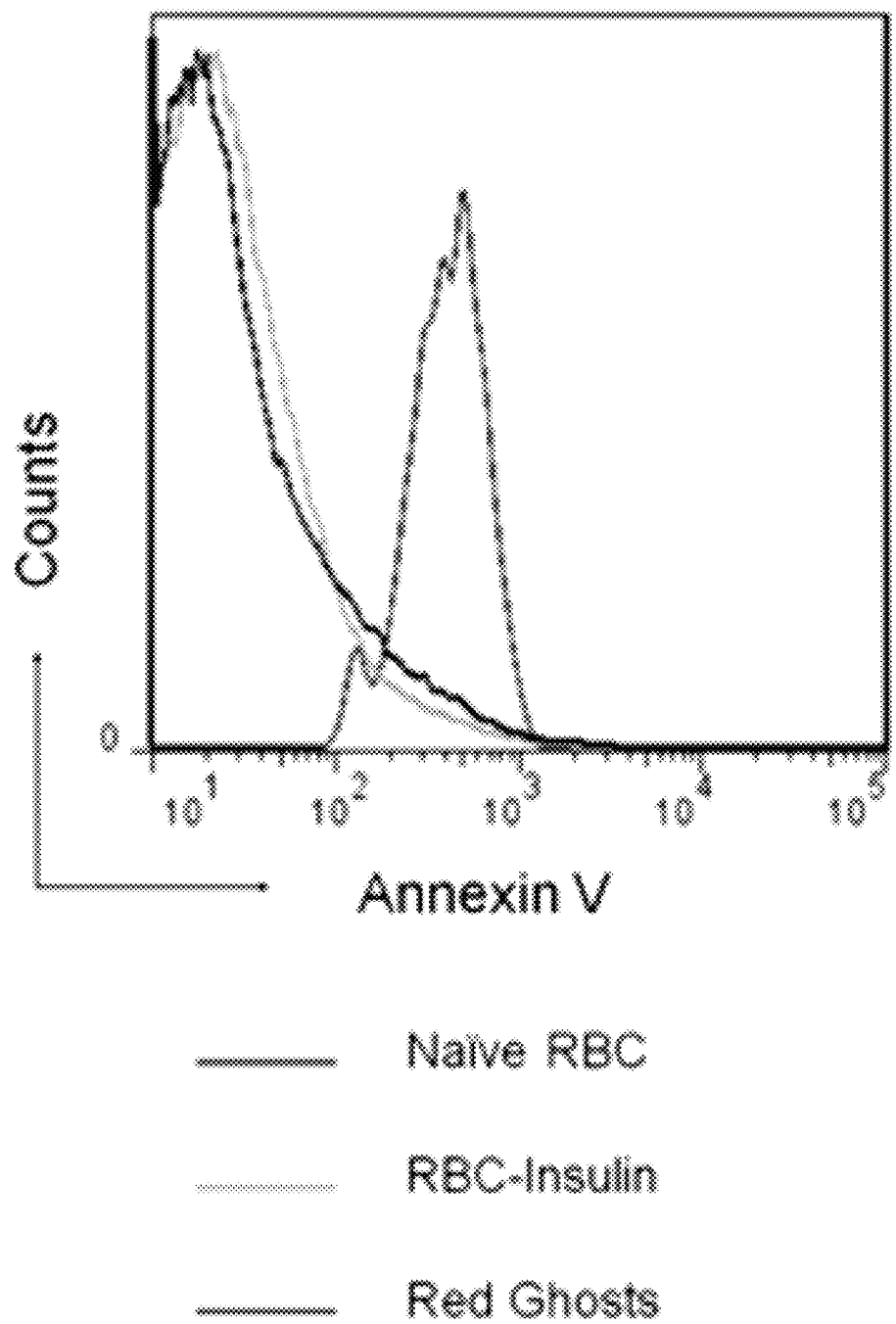
FIG. 6A shows the histogram data of flow cytometry results of naïve mRBCs, mRBCs loaded with glucose-insulin conjugates, and red ghost stained with FITC-annexin V. Red ghost is the positive control obtained by using lysing buffer (5 mM $NaH_2PO_3/Na_2HPO_3$, pH8) incubated for 5 min at 4° C.
Figure 6B:
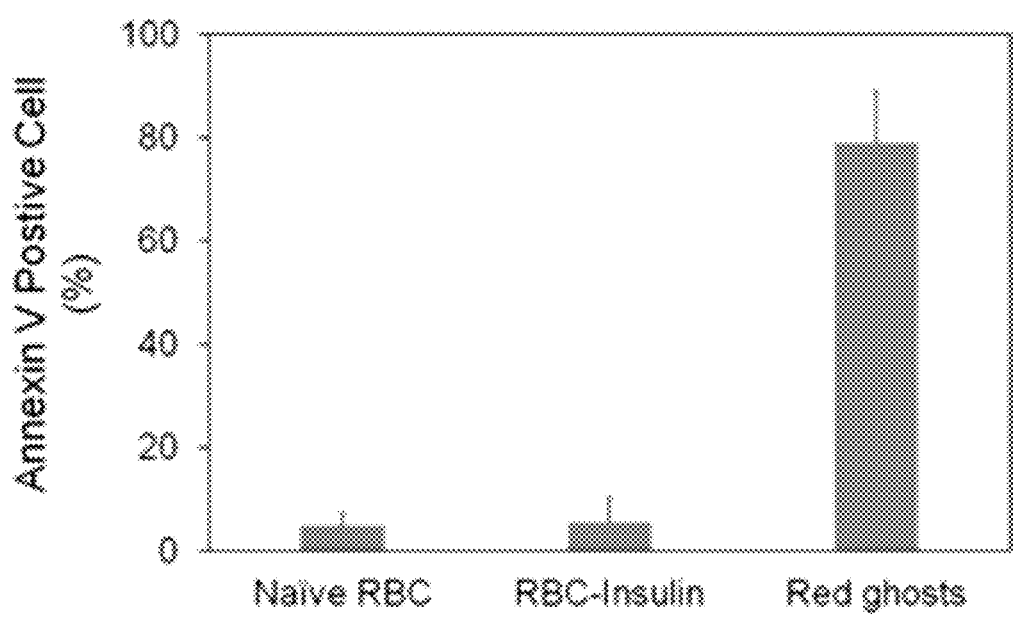
FIG. 6B shows a bar graph summary of the flow cytometry results shown in FIG. 6A.

GLUTs are membrane proteins that facilitate the transport of glucose down a concentration gradient through the plasma membrane (Mueckler, M. Eur. J. Biochem. 219, 713-725 (1994)). Glucose transporter 1 (GLUT1) is the main glucose transporter on human RBCs; while glucose transporter 4 (GLUT4) is the dominant glucose transporter in RBCs of adult mice (Vrhovac, I, et al. Period. Biol. 116, 131-138 (2014); Montel-Hagen, A, et al. Curr. Opin. Hematol. 16, 165-172 (2009); Montel-Hagen A, et al. Blood 112, 4729-4738 (2008)). The mRBCs were incubated with Glu-Insulin overnight and imaged using the confocal fluorescence microscope to determine whether Glu-Insulin can bind to mRBCs via the specific glucose-GLUT binding. As predicted, Glu-Insulin bound to the mRBCs (FIG. 5A). In addition, the signals of insulin and GLUT4 were well co-localized on the mRBCs membrane. The flow-cytometry results further indicated that the attachment of Glu-Insulin toward mRBCs was via the specific Glucose-GLUT interaction. With the glucose modification, insulin more easily attaches to mRBCs than native insulin. Additionally, in the presence of excess free glucose, the amount of binding Glu-Insulin to mRBCs is decreased (FIG. 5B). The loaded insulin to mRBCs was determined by the ELISA assay. mRBCs could be readily coupled with Glu-Insulin up to $5*10^{-13}$ g per cell. Furthermore, the annexin V binding assay confirmed that insulin binding does not cause significant damage to mRBCs (FIG. 6A-B).

Figure 5C:
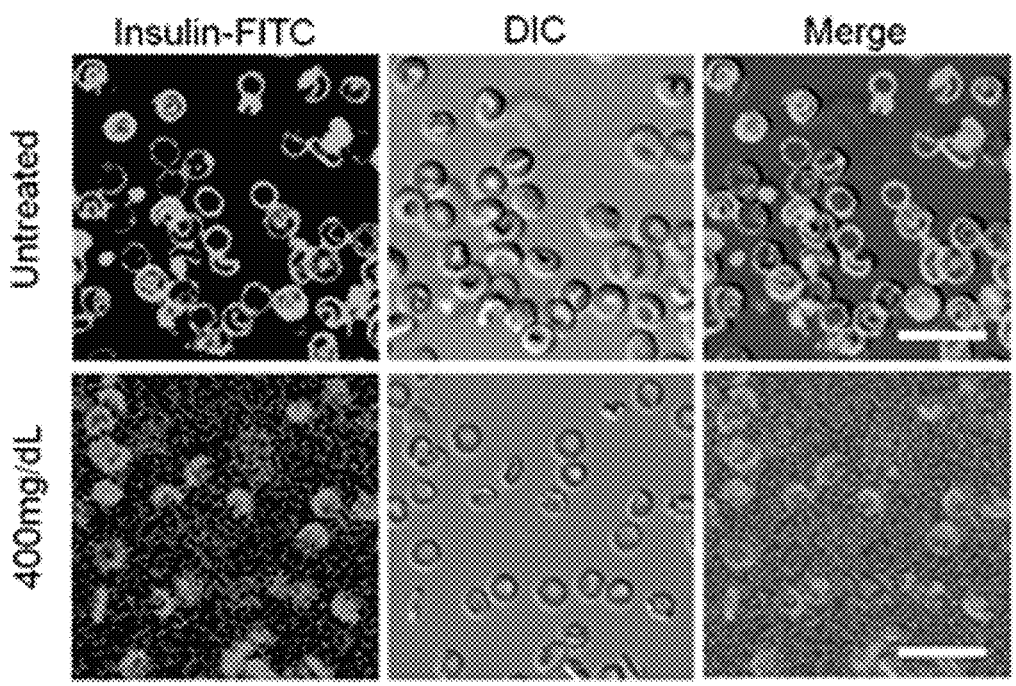
FIG. 5C shows confocal microscopy images of the Glu-insulin attached mRBCs untreated and treated with 400 mg/dL glucose solution. (Scale bar=50 μm).
Figure 5D:
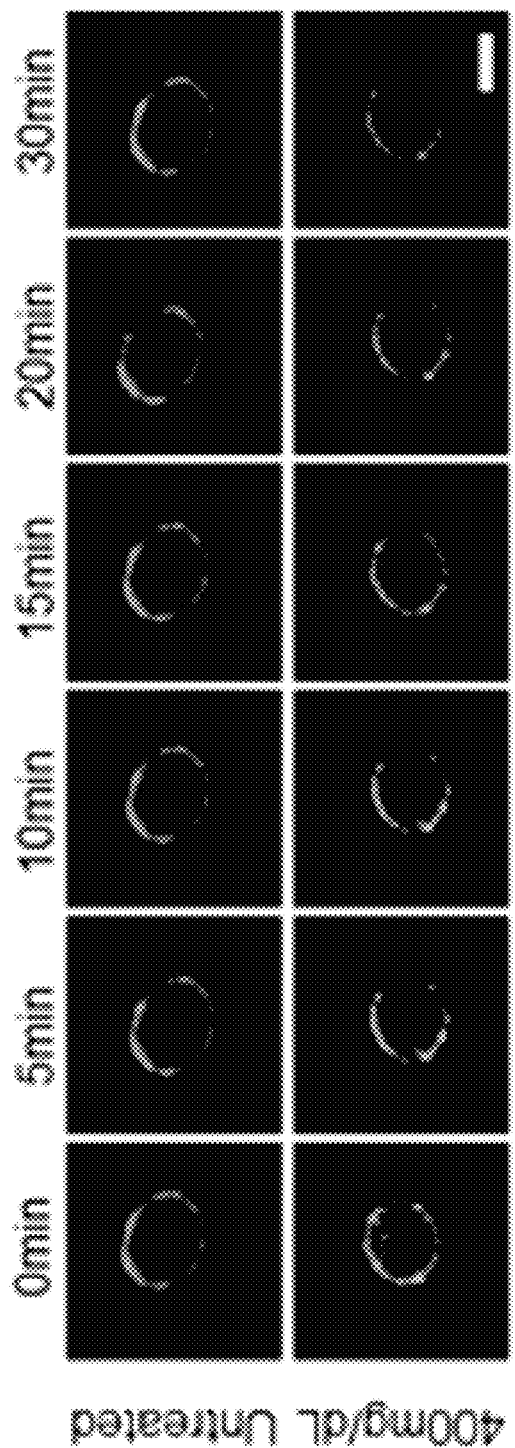
FIG. 5D shows confocal microscopy images of the single Glu-insulin attached mRBC treated with 400 mg/dL glucose solution at different time points. (Scale bar=5 μm).
Figure 5E:
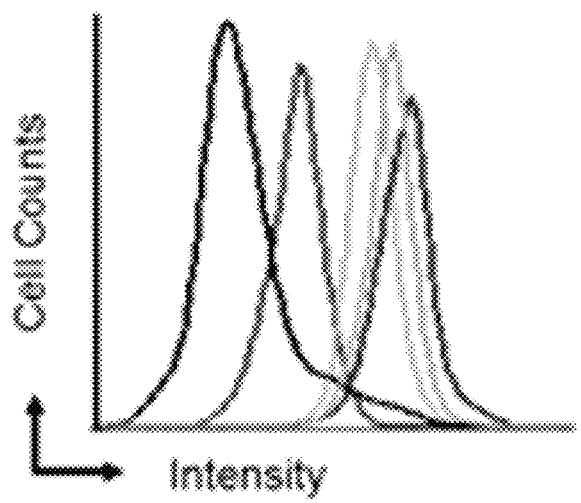
FIG. 5E shows flow cytometry data of insulin attached mRBCs treated with different concentrations of glucose solutions.
Figure 5F:
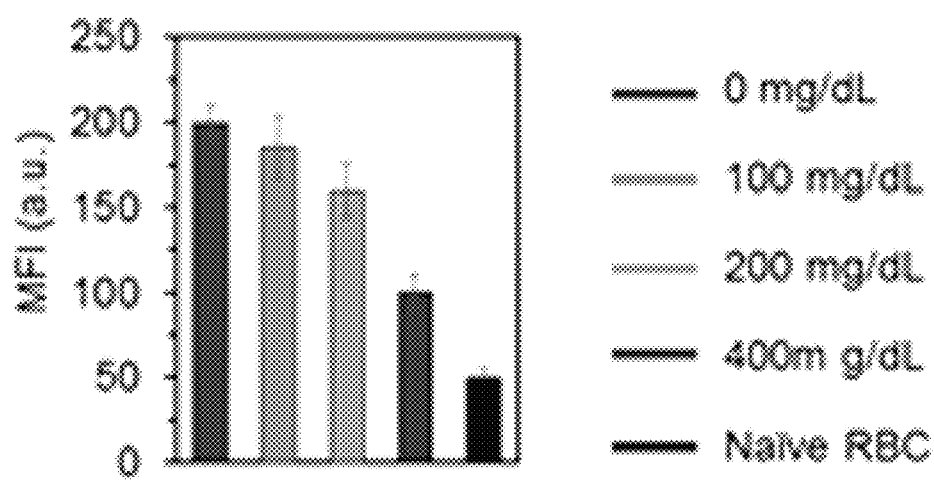
FIG. 5F shows a corresponding mean fluorescent intensity (MFI) quantification of FITC-insulin-mRBCs.
Figure 5G:
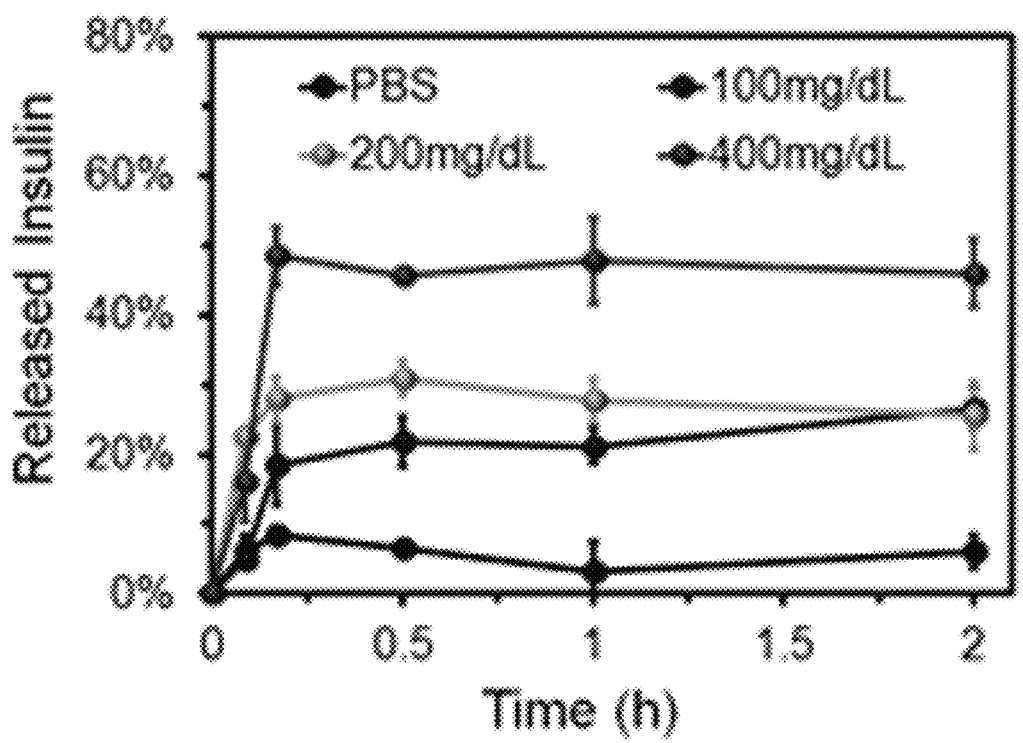
FIG. 5G shows the in vitro accumulated Glu-insulin release from the mRBCs in several glucose concentrations as indicated at 37° C.

To examine the glucose-responsive insulin release performance, Glu-fluorescein (FITC)-insulin attached mRBCs were incubated in PBS containing different concentrations of glucose. As observed in confocal imaging (FIG. 5C-D), compared to untreated insulin-mRBCs, the fluorescence signals of insulin on the mRBCs membrane were notably decreased after 30 min when treated with 400 mg/dL glucose in PBS, due to the detachment of the insulin from mRBCs (FIG. 5C). Moreover, single insulin loaded mRBC was tracked and observed over time in confocal imaging. As expected, when treated with 400 mg/dL glucose in PBS, fluorescence signals of insulin on the mRBCs membrane decreased over 30 min compared with untreated insulin-mRBC (FIG. 5D). The flow-cytometry results further substantiated that the signals of insulin on mRBCs decreased with increased glucose concentration. Only approximately 50% less insulin signals was detected on 400 mg/dL glucose treated mRBCs (FIG. 5E-F). Next, the insulin release profiles in response to varying glucose levels were assessed, including a typical hyperglycemic level (400 mg/dL), normoglycemic levels (100 and 200 mg/dL), and a control level (0 mg/dL). The released amounts of insulin from mRBCs were determined by the ELISA assay. As shown in FIG. 5G, about 50% of insulin is released from mRBCs incubated with 400 mg/dL glucose within 2 h, significantly higher than samples associated with normal glucose levels. These results are also consistent with the flow cytometry data mentioned above.

Figure 5H:
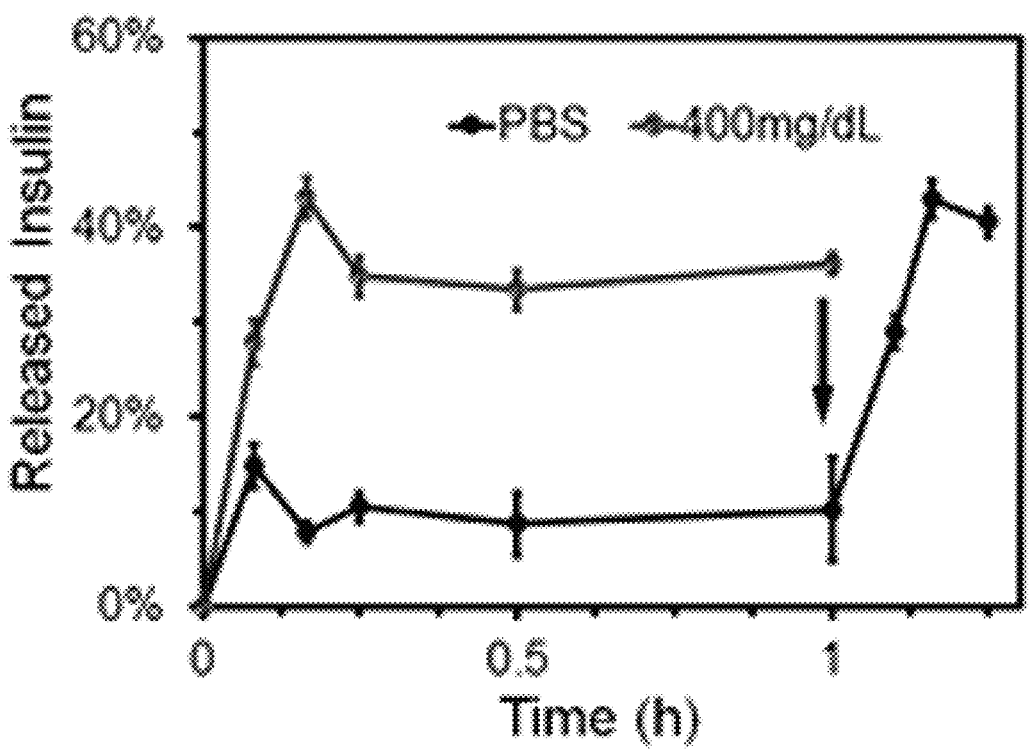
FIG. 5H shows the in vitro accumulated Glu-insulin release from the mRBCs. The black arrows indicate the administration points.
Figure 5I:
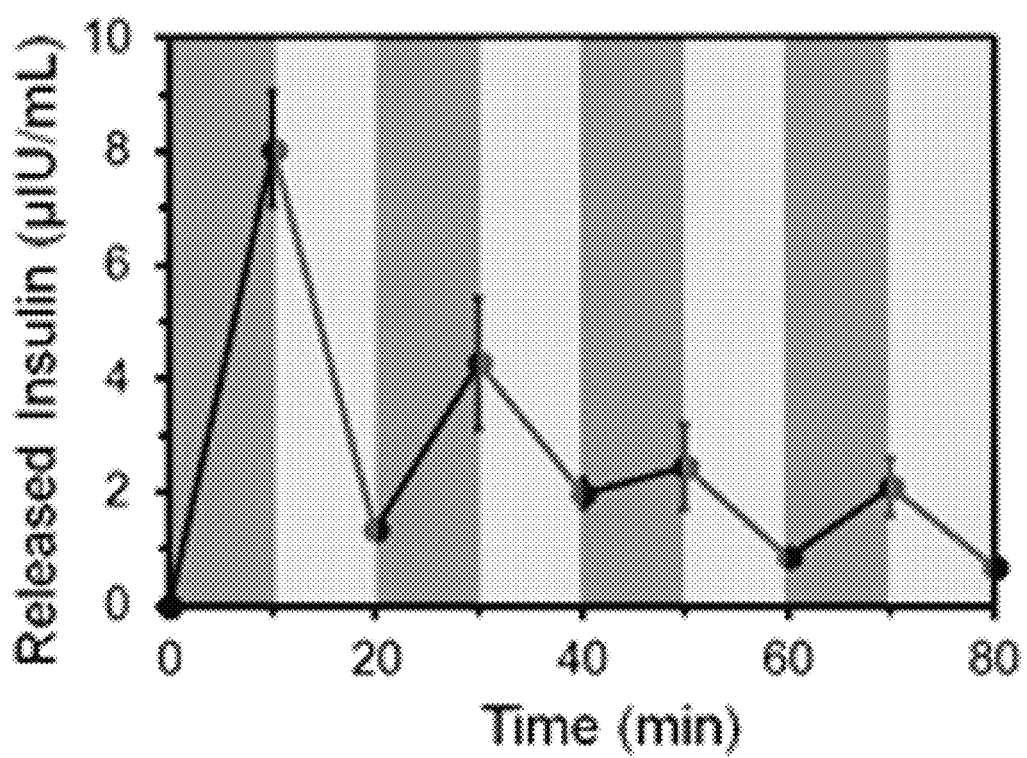
FIG. 5I shows the pulsatile Glu-insulin release profile of mRBCs.

Importantly, the quick release of insulin after exposure to high glucose was documented (FIG. 5H), suggesting the potential for clinical effectiveness. Furthermore, pulsatile release kinetics of insulin was achieved when the glucose concentration was periodically varied between the normal and hyperglycemic levels for several cycles (FIG. 5I). The release rates increased to a maximum within the first 10 min and then gradually decreased, which can be attributed to the gradual depletion of Glu-Insulin interacting with GLUTs.

Example 2. In Vivo Studies of Glucose-Responsive Insulin Delivery Using RBCs

Figure 7A:
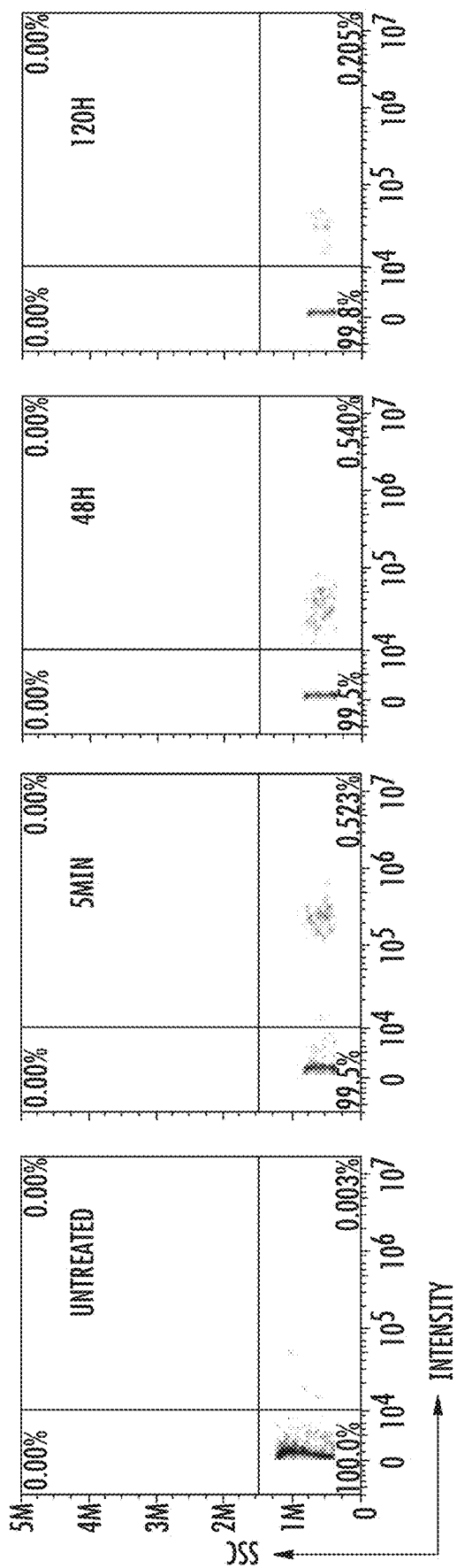
FIG. 7A shows the results of a flow cytometry experiment to determine the percentages of engineered mRBC-insulin (positive in FITC) in the blood samples.
Figure 7B:
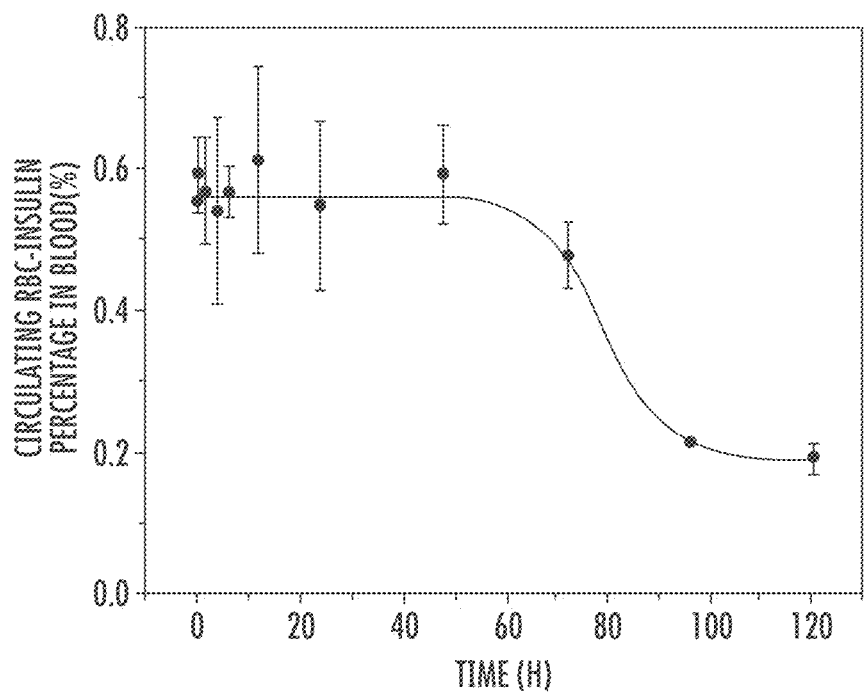
FIG. 7B shows blood-circulation curves of insulin–mRBCs in mice. The percentages of RBC (injected) among total collected mRBCs appeared to be stable even 72 hours after injection. Error bars are based on the SD of triplicated samples.

Next, glucose-responsive performance of Glu-Insulin conjugated mRBCs (insulin-mRBCs) was examined in vivo. To assess the blood-circulation behavior of the cell carrier, mRBCs coupled with FITC ($5\times10^7$ RBCs in 500 μL PBS) were loaded with Glu-Insulin and then i.v. injected into healthy mice. About 3 μL of blood was extracted from the tail at different time points and then dispersed in 0.5 mL PBS with anticoagulants. Flow cytometry measurement was applied to determine the percentage of insulin-mRBC (positive in FITC) in the blood samples. The percentage of mRBC (injected) among total collected mRBCs appeared to be stable even 72 h after injection (half-life=85.6 h), suggesting stability of insulin-mRBCs (FIG. 7A-B).

Figure 8A:
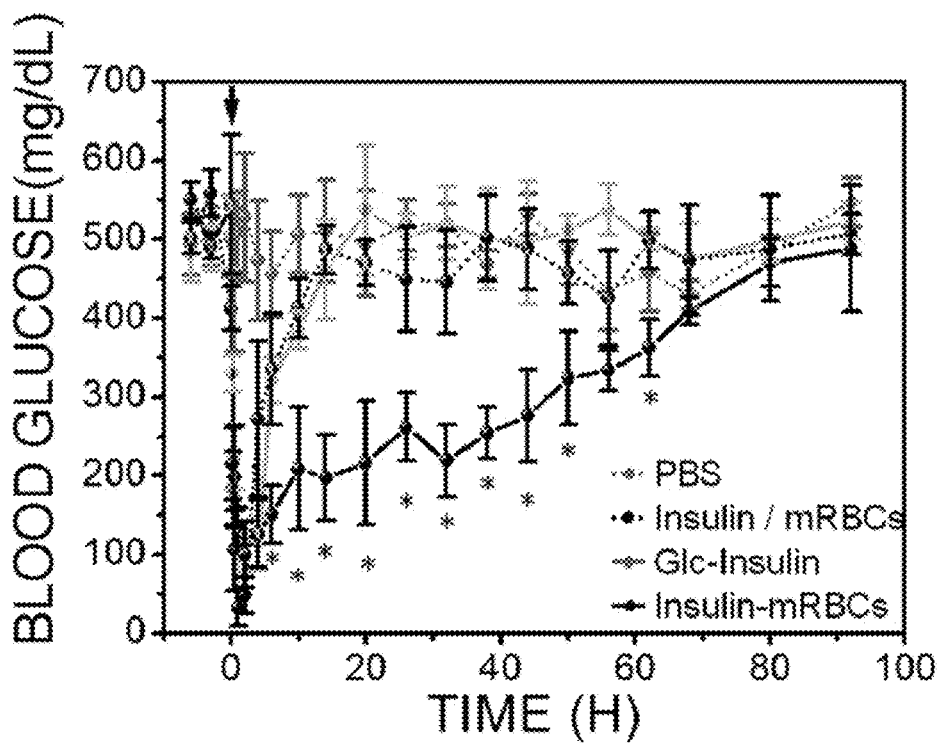
FIG. 8A shows BG levels in STZ-induced diabetic mice after treatment with free insulin+mRBCs, Glu-Insulin, insulin–mRBCs and PBS control. The black arrow indicates the administration time.

The efficacy of insulin-mRBCs for treatment of hyperglycemia in STZ-induced type 1 diabetic mice (Like, A A, et al. Science 193, 415-417 (1976)) was also assessed. Groups of animals were treated by i.v. injection with insulin-mRBCs, free insulin plus mRBCs, Glu-Insulin alone and PBS control (each at a dose of 5 mg/kg insulin or volume control). The BG levels of treated mice were then monitored over time. As shown in FIG. 8A, for mice treated with free insulin plus mRBCs and with Glu-Insulin, the BG levels declined steadily to hypoglycemic within 1 h (<70 mg/dL) and recovered to hyperglycemic range (~500 mg/dL) quickly within 24 h. In contrast, the BG level in mice treated with insulin-mRBCs decreased and maintained at about 200 mg/dL at least 24 h and increased gradually over 4 days, demonstrating high stability of the mRBCs carriers in the circulation with ongoing glucose-dependent insulin release.

Figure 8B:
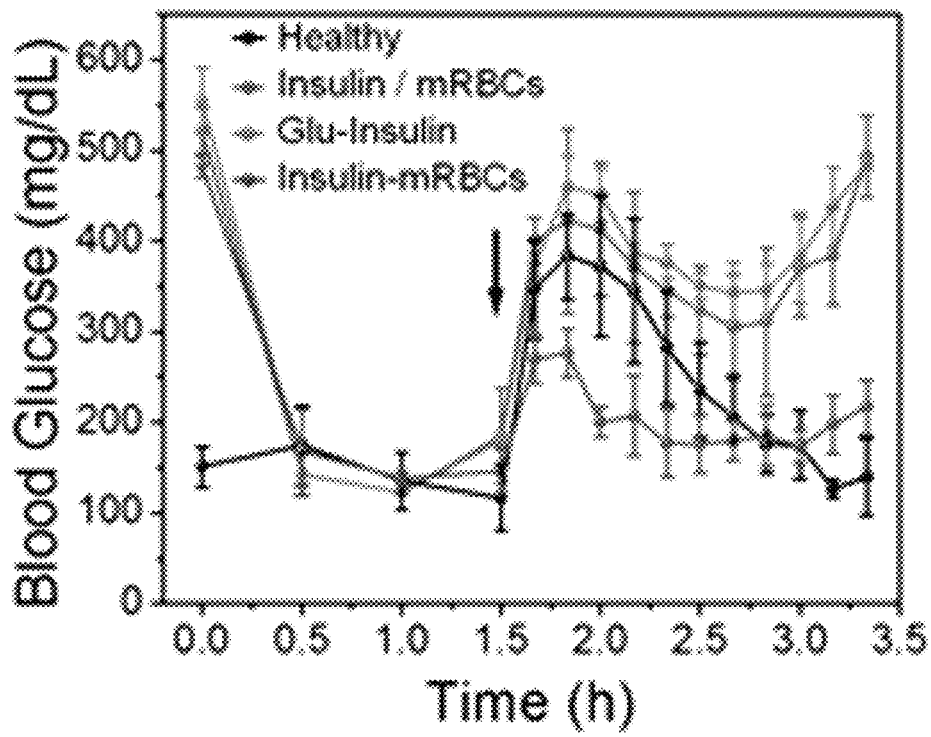
FIG. 8B shows the results of an in vivo glucose tolerance test in STZ-diabetic mice. The insulin–mRBCs i.v. was injected at time 0 and an IPGTT performed 1.5 hours following insulin administration. The black arrows indicate the administration points.
Figure 8C:
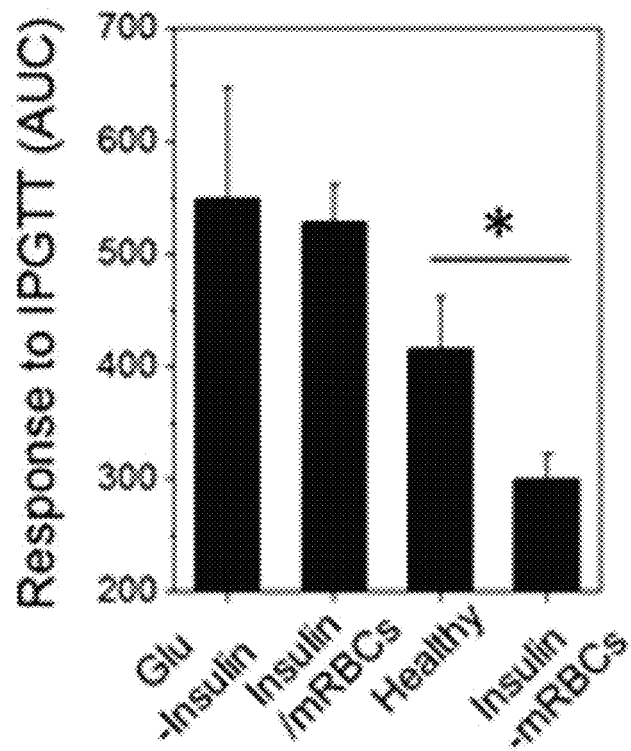
FIG. 8C shows responsiveness data, which was calculated based on the area under the curves of FIG. 8B, from 90 to 200 minutes. The baseline was set at the 90-minute BG reading.
Figure 8D:
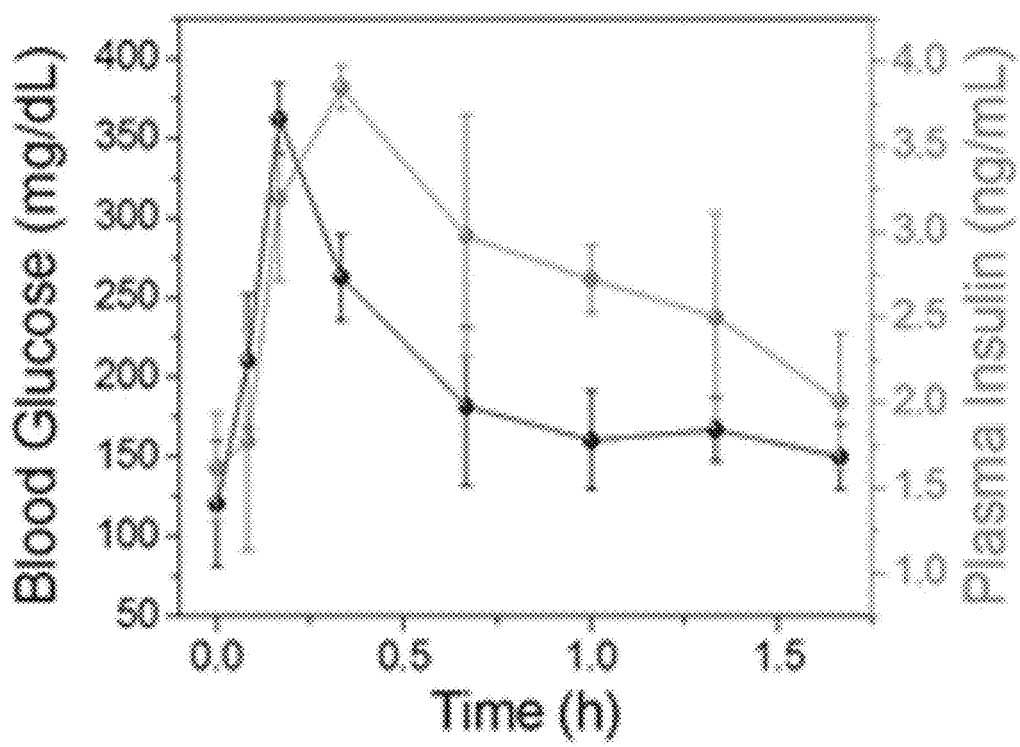
FIG. 8D shows the change in plasma insulin levels and glucose levels after IPGTT.

To further understand the dynamics of insulin release in vivo, intraperitoneal glucose tolerance tests (IPGTT) were performed 1.5 hours after administration of the insulin-mRBCs (FIG. 8B). As shown, following the IPGTT, the control healthy mice exhibited a quick increase in BG level and recovery to a normal BG level within 2 hours. In diabetic mice, BG levels of insulin-mRBCs treated mice show a delayed increase in BG level, then decline to approximately 200 mg/dL and maintained a normoglycemic state within 2 hours. In STZ-diabetic mice treated with free insulin+mRBCs or with Glu-Insulin, BG levels only exhibited a fleeting response. To quantitate the glucose response to the various insulin formulations (Yu J, et al. Proc. Natl. Acad. Sci. U.S.A. 112, 8260-8265 (2015); Chou DH-C, et al. Proc. Natl. Acad. Sci. U.S.A. 112, 2401-2406 (2015)), the area under the curve was calculated for each group between 90 and 200 min. Insulin-mRBCs treated mice show enhanced responsiveness to IPGTT as compared to free insulin treated mice (FIG. 8C). Furthermore, plasma insulin levels of diabetic mice were monitored over time by ELISA after IPGTT (FIG. 8D). As BG levels increased, the serum insulin level followed closely both in the rise of glucose and on its fall to normal.

Figure 8E:
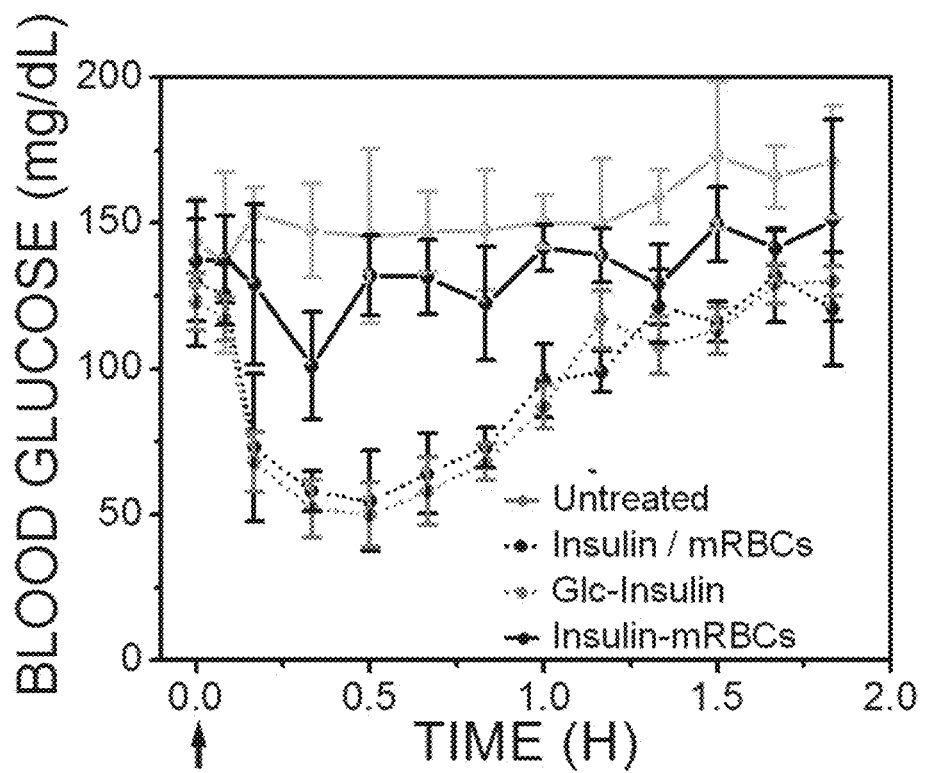
FIG. 8E shows the BG changes of healthy mice administered by insulin-mRBCs over time. The black arrows indicate the administration points.
Figure 8F:
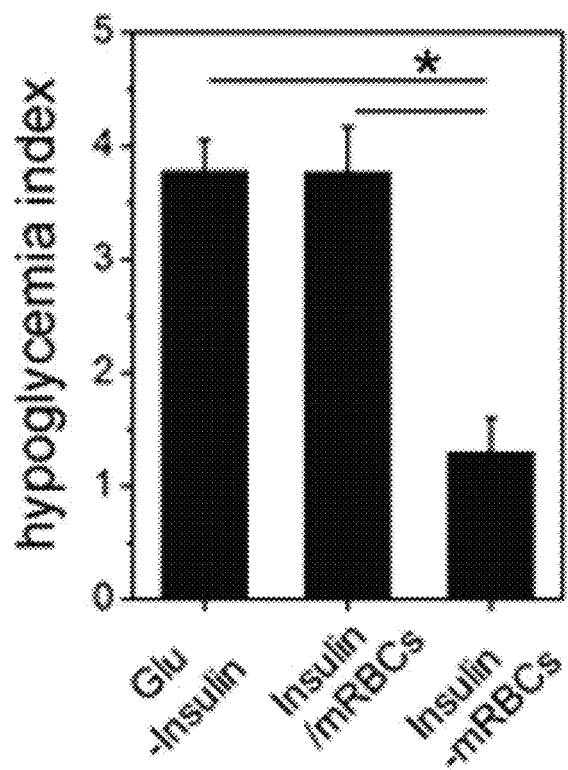
FIG. 8F is a bar graph showing the quantification of the hypoglycemia index, calculated from the difference between the initial and nadir BG readings divided by the time at which nadir was reached. The error bars are based on the SD of five mice per group. (P values: *P<0.05)

Next, the potential for insulin-mRBCs to induce hypoglycemia was studied in healthy mice under normoglycemic conditions (FIG. 8E). As shown, native insulin+mRBCs and Glu-Insulin treated mice show significantly decreased BG levels compared to insulin-mRBCs treated mice (insulin, 1 mg/kg). The corresponding hypoglycemia index was calculated to assess the risk of hypoglycemia (Yu J, et al. Proc. Natl. Acad. Sci. U.S.A. 112, 8260-8265 (2015); Chou DH-C, et al. Proc. Natl. Acad. Sci. U.S.A. 112, 2401-2406 (2015)). Treatment with insulin-mRBCs significantly reduced hypoglycemic index compared to control groups (FIG. 8F).

Figure 9:
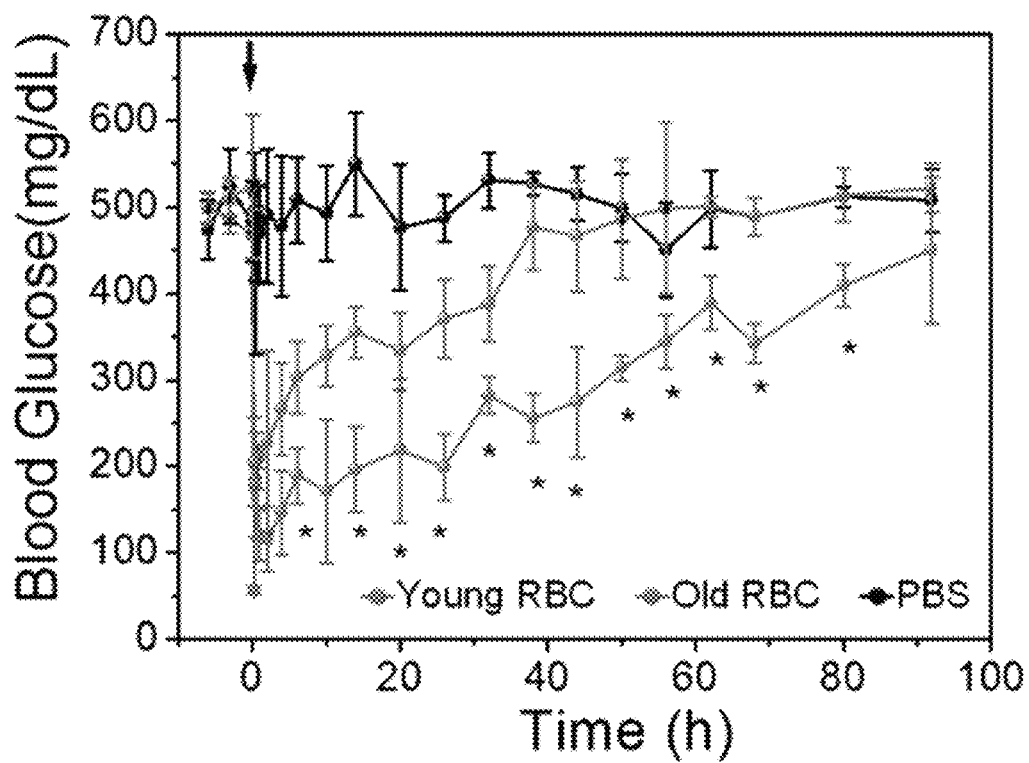
FIG. 9 is a comparison of young and old red blood cells as carriers for insulin delivery. The black arrows indicate the administration points.

Red blood cell vehicles from young (4 weeks) versus old (1 year) mice were compared with respect to their insulin delivery capabilities (FIG. 9). Interestingly, young mRBCs had a more effective and longer anti-diabetes efficacy than old mRBCs. This result may be due to the more stable and longer life span of the young mRBCs than aged mRBCs in circulation (Shemin, D, et al. J. Biol. Chem. 166, 627-636 (1946)).

Figure 11:
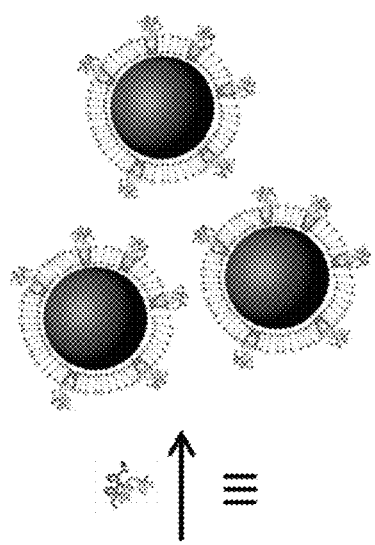
FIG. 11 is a schematic of the fabrication of insulin-PLGA-RM nanoparticles. I, isolation of RBC membranes. II, coating RM to PLGA nanoparticles. III, binding of Glu-Insulin to PLGA-RM nanoparticles.
Figure 11:
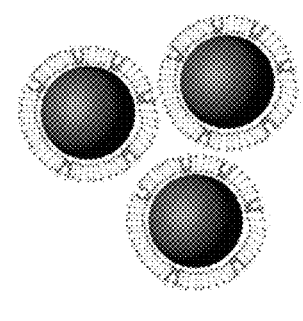
Figure 11:
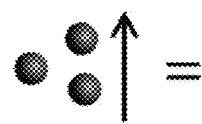
Figure 11:
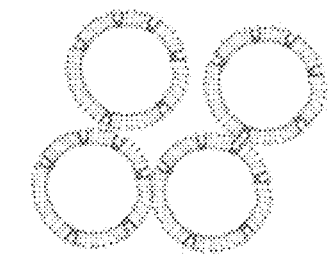
Figure 11:
Figure 11:
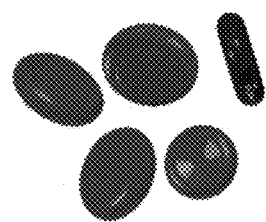
Figure 12A:
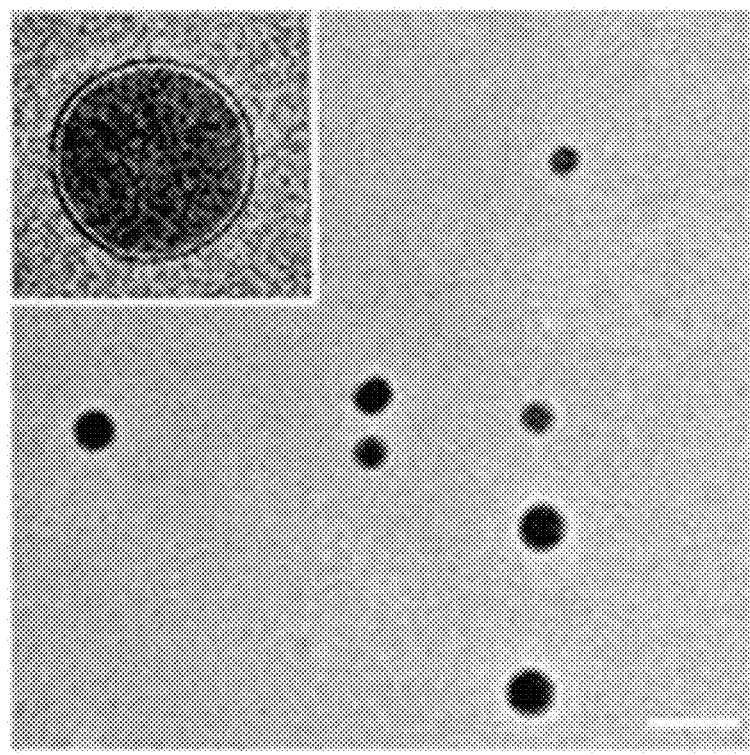
FIG. 12A shows TEM images of PLGA-RM nanoparticles. Inset: zoom-in image. (Scale bar=200 nm).
Figure 12B:
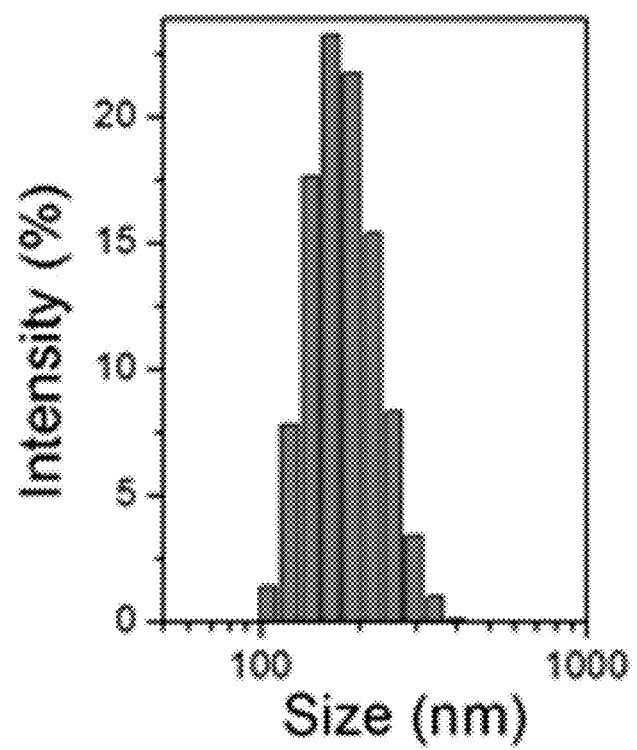
FIG. 12B shows dynamic light scattering (DLS) characterization of PLGA-RM nanoparticles.
Figure 12C:
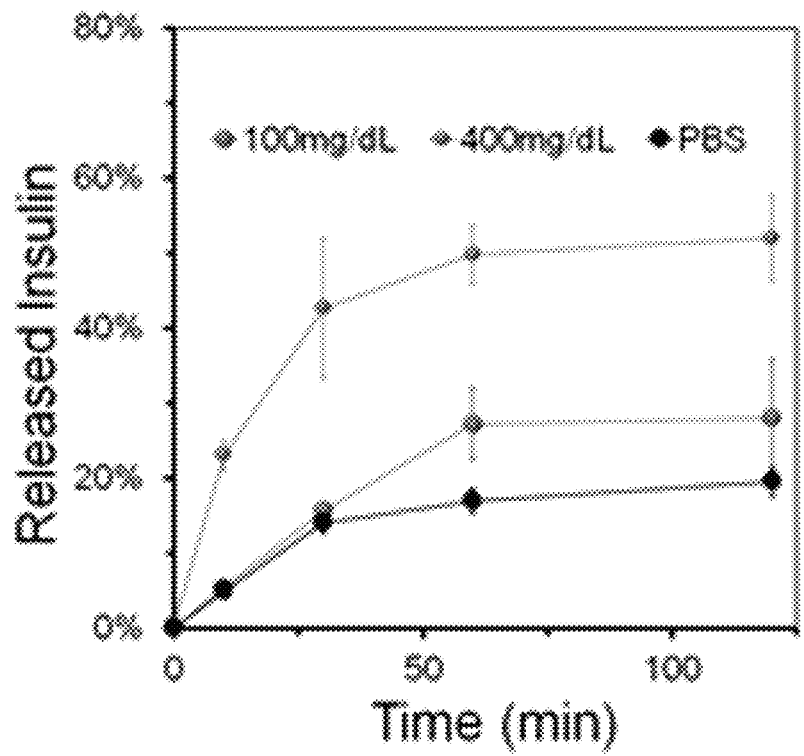
FIG. 12C shows in vitro accumulated insulin release from the PLGA-RM in several glucose concentrations as indicated at 37° C.
Figure 12D:
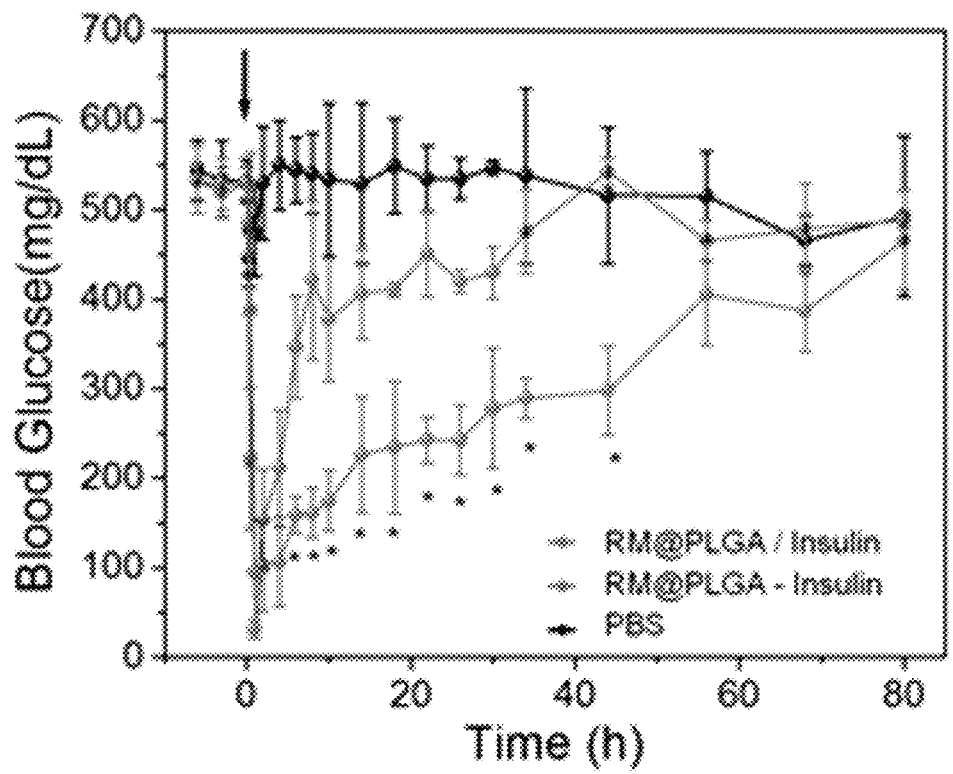
FIG. 12D shows in vivo BG levels in STZ-induced diabetic mice after treatment with free insulin+PLGA-RM NPs, insulin-PLGA-RM NPs and PBS control. The black arrows indicate the administration points.
Figure 12E:
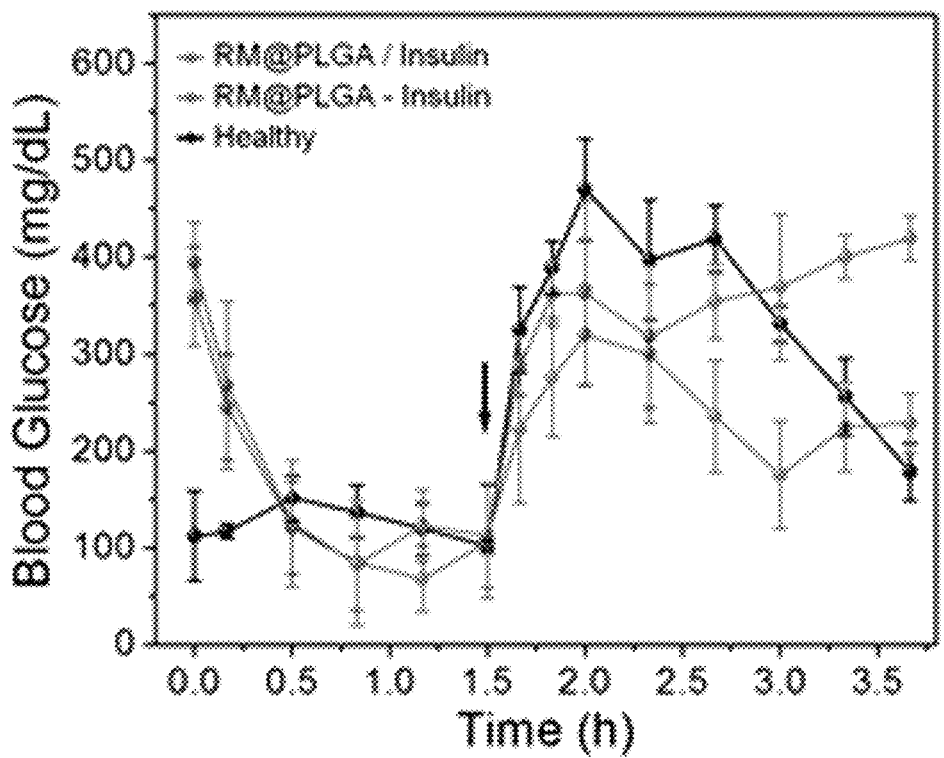
FIG. 12E shows in vivo glucose tolerance test toward diabetic mice. With the insulin-PLGA-RM nanoparticles i.v. injected at time 0 and an IPGTT performed 1.5 hours following insulin administration. The black arrows indicate the administration points.
Figure 12F:
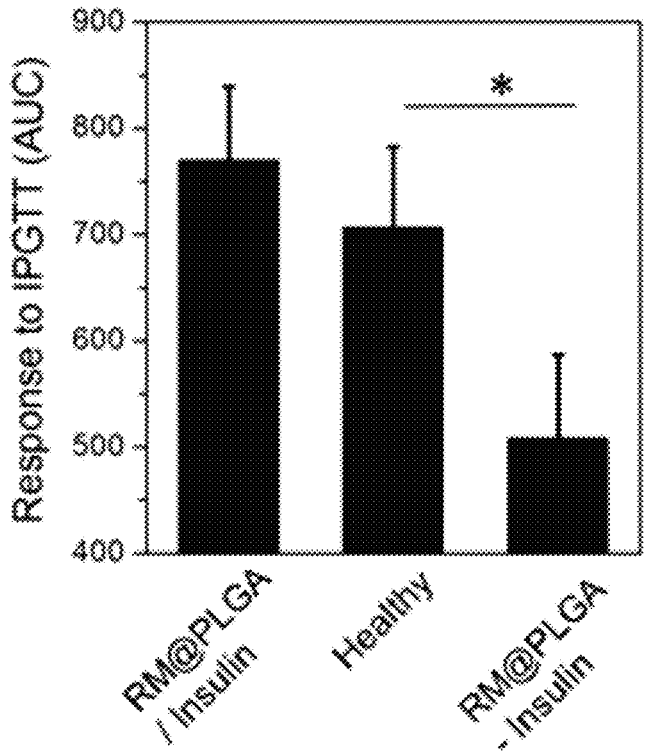
FIG. 12F shows responsiveness data. Responsiveness was calculated based on the area under the curve (AUC) in 120 minutes, with the baseline set at the 90-min BG reading.
Figure 12G:
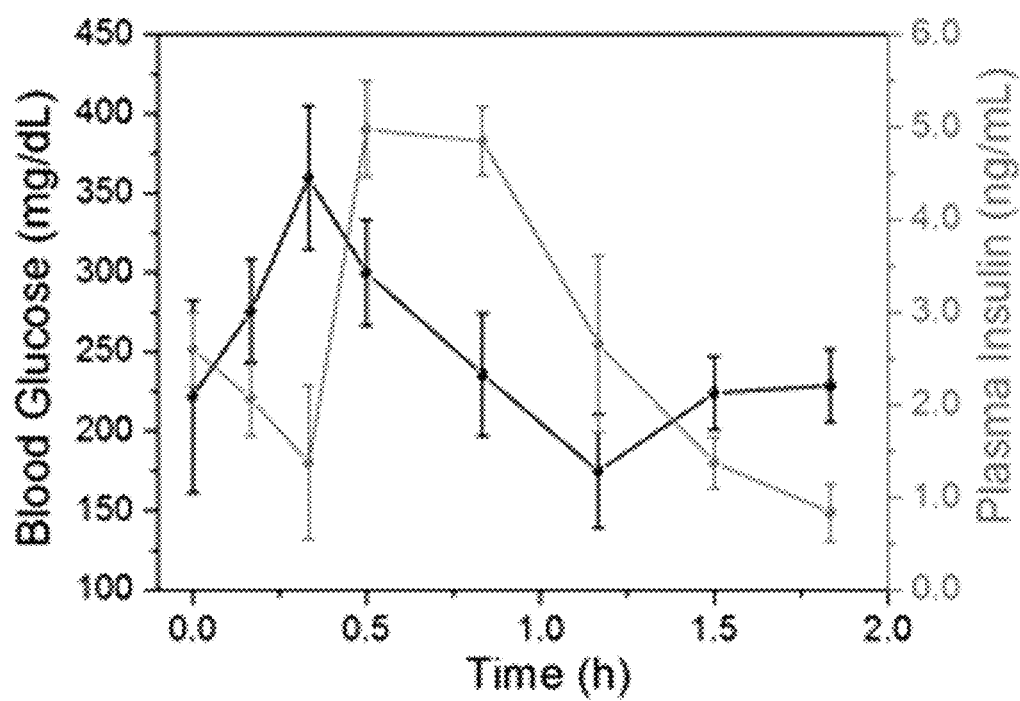
FIG. 12G shows the change in plasma insulin levels and glucose levels after IPGTT. The error bars are based on the standard deviation (SD) of five mice per group. (P values: *P<0.05)
Figure 13B:
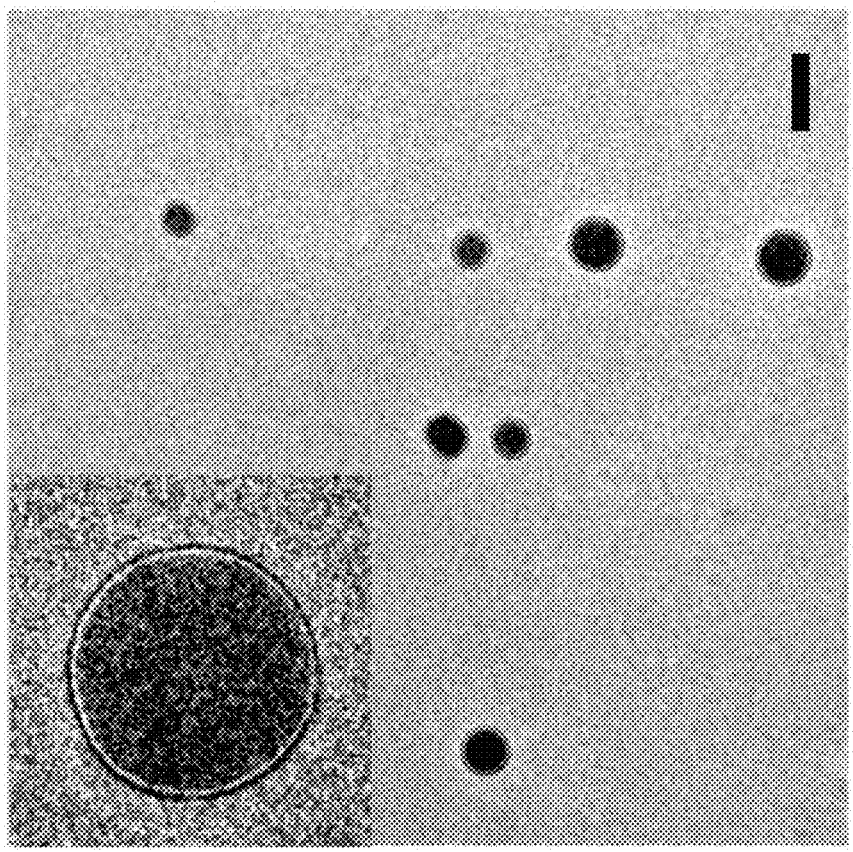
FIG. 13B shows TEM images of PLGA NPs after mRBCs membranes modification.
Figure 13A:
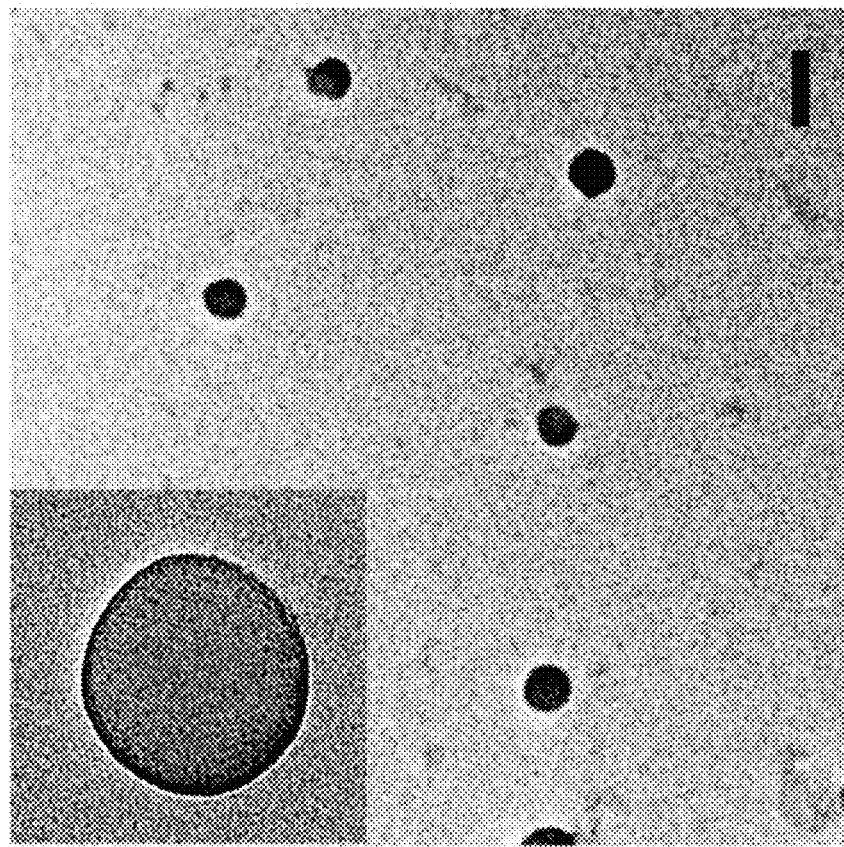
FIG. 13A shows TEM images of PLGA NPs before mRBCs membranes modification.
Figure 13D:
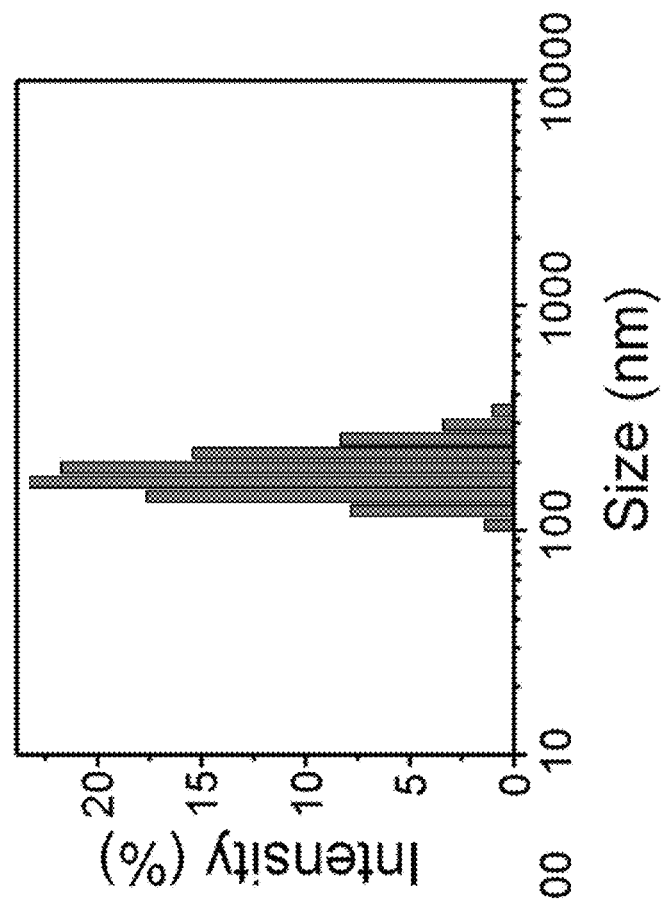
FIG. 13D shows dynamic light scattering (DLS) of PLGA NPs after mRBCs membranes modification. PLGA NPs showed slightly increased DLS measured diameter from 145 nm to 160 nm. (Scale bar=200 nm) (comparing FIG. 13C to FIG. 13D).
Figure 13C:
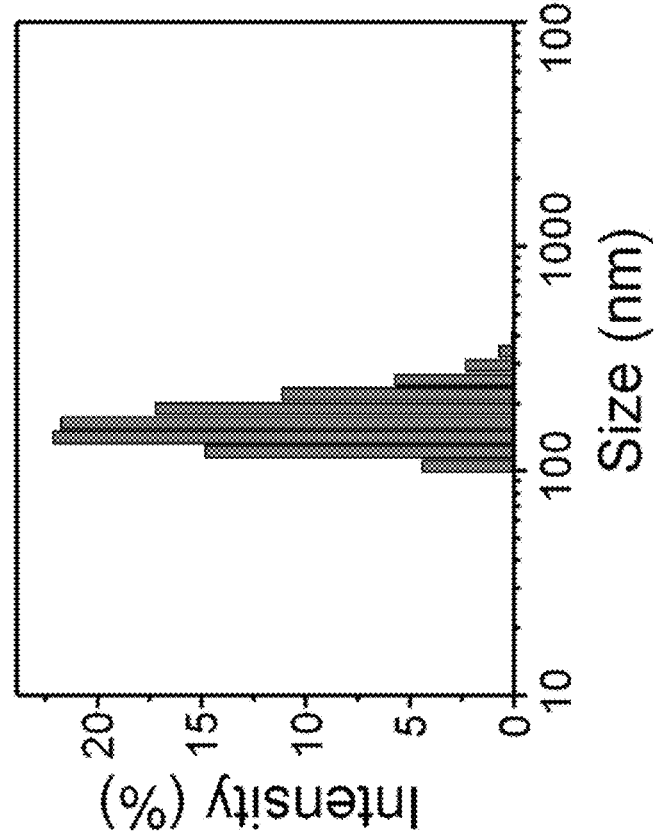
FIG. 13C shows dynamic light scattering (DLS) of PLGA NPs before mRBCs membranes modification.
Figure 14:
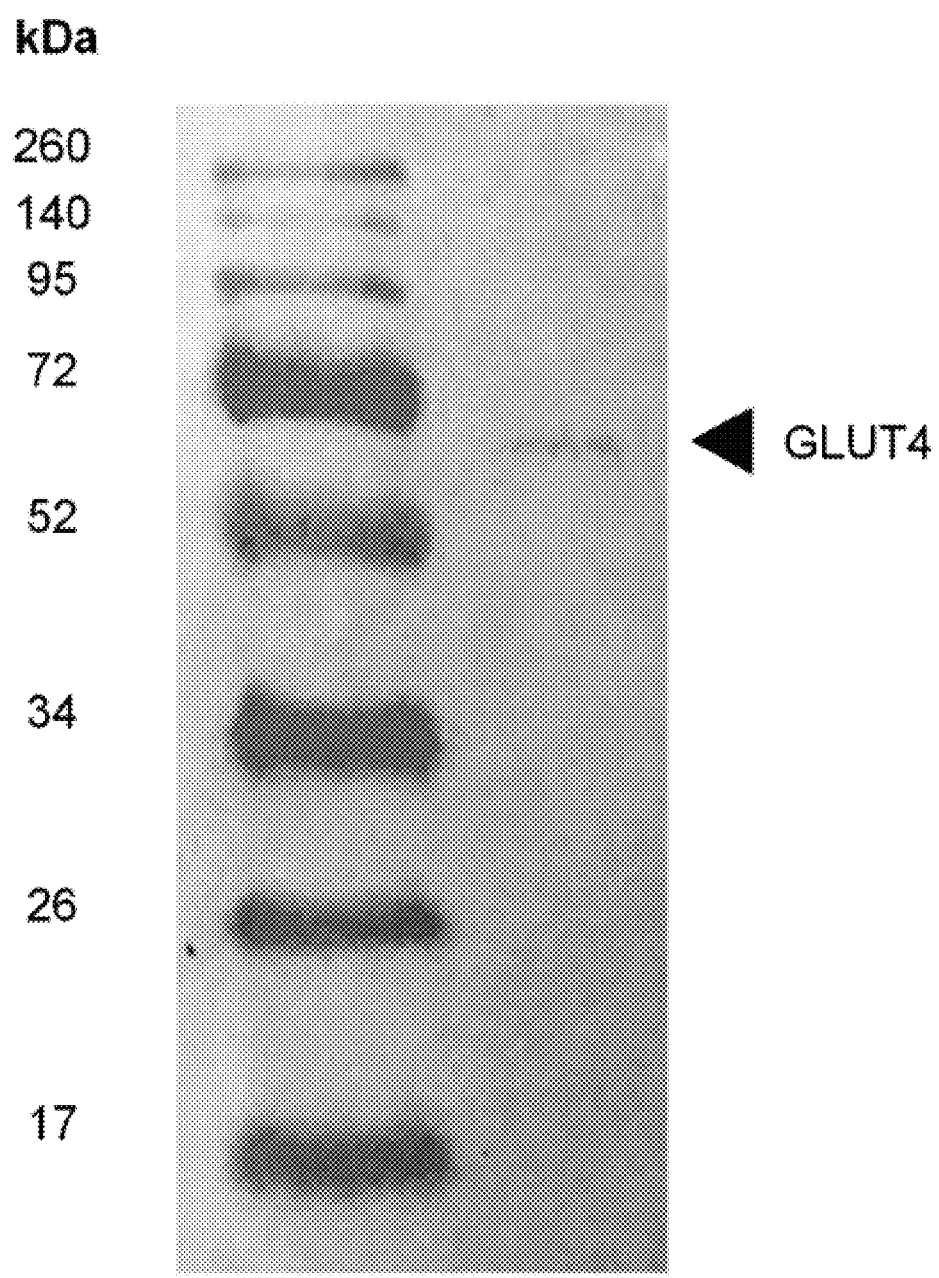
FIG. 14 shows the results of a western blot conducted to verify that GLUT4 existed on the RM coated PLGA NPs. As shown, only one band of approximately 60 kDa in size was visible on the nitrocellulose (NC) membrane.
Figure 15:
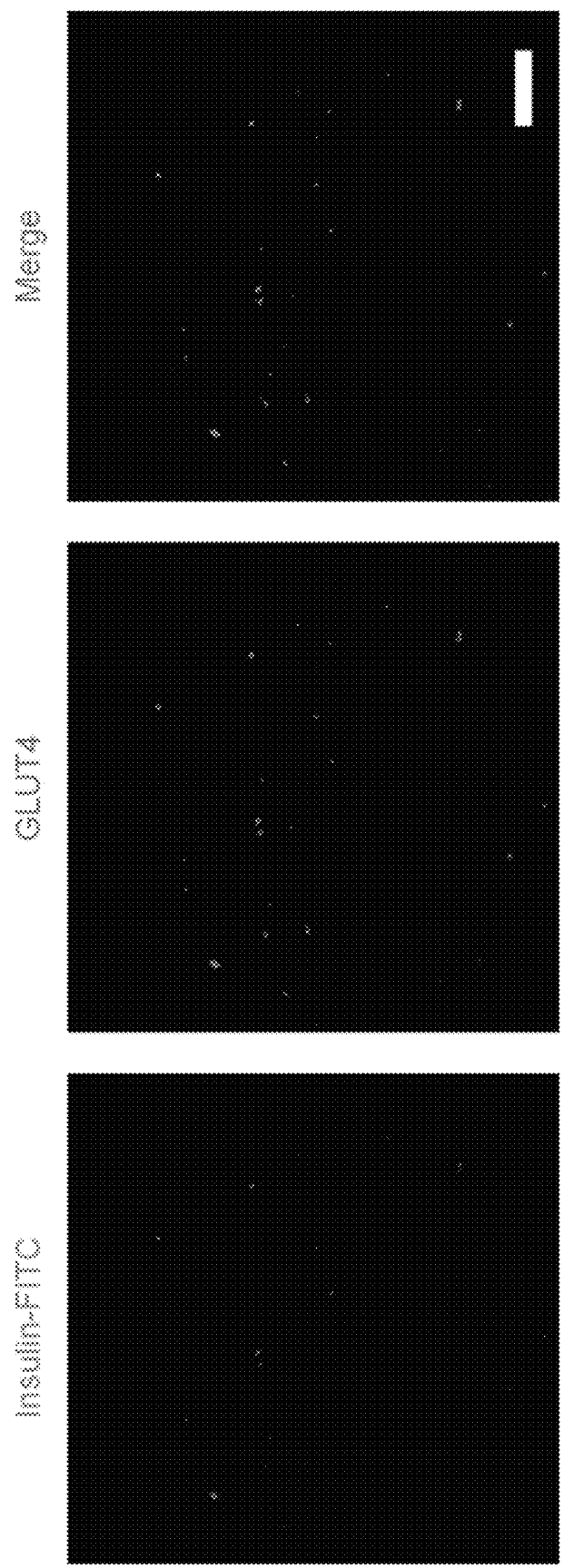
FIG. 15 shows confocal microscopy images of the insulin attached RM-PLGA NPs. Insulin and GLUT4 signals were co-localized. (Scale bar=10 μm)
Figure 16A:
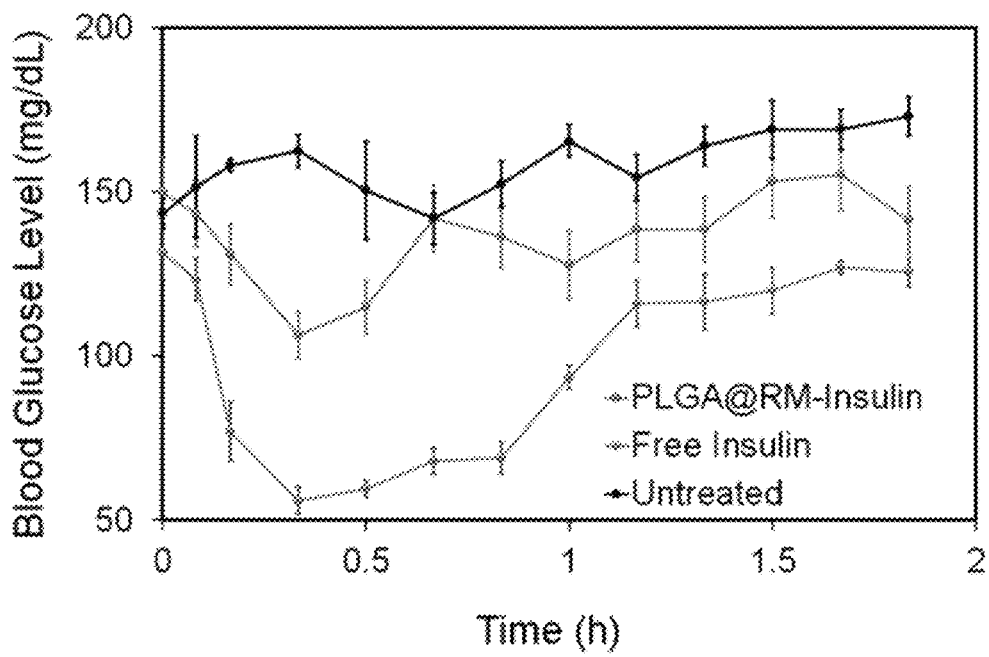
FIG. 16A shows the blood glucose changes of healthy mice administered by insulin-RM-PLGA NPs over time.
Figure 16B:
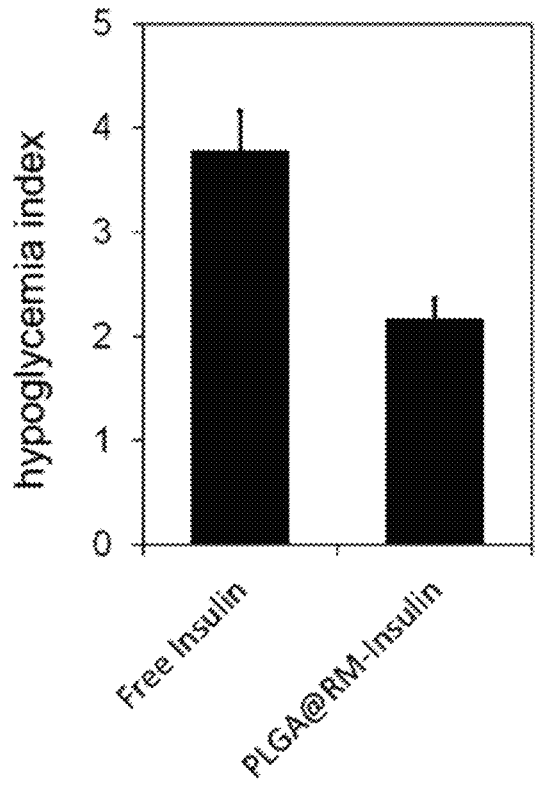
FIG. 16B shows the quantification of the hypoglycemia index, which was calculated from the difference between the initial and nadir blood glucose readings shown in FIG. 16A, divided by the time at which nadir was reached. The error bars are based on the standard deviation (SD) of five mice per group. (P values: *P<0.05)

Example 3. Glucose-Responsive Insulin Delivery from RBC Membrane-Coated PLGA Nanoparticles PLGA nanoparticles were fabricated and were coated with mRBC membranes (RM). FIG. 11 shows a schematic of the synthesis process. The obtained RM-PLGA nanoparticles were monodispersed, as revealed by the transmission electron microscopy (TEM) and dynamic light scattering (DLS). The TEM images show that most of PLGA NPs are well coated with mRBC membranes with a diameter of 100 nm (FIGS. 12A-B and 13A-B). After RM coating, PLGA NPs display a slight increase in the DLS measured diameter from 145 nm to 160 nm (FIGS. 13C-D). Western blot analysis was conducted to verify that GLUT4 is present on the RM coated PLGA NPs (FIG. 14). Next, Glu-Insulin was attached to RM-PLGA NPs, likely via the specific glucose-GLUT interaction. The attachment (loading capacity: 2%) was also confirmed by confocal imaging (FIG. 15) and an ELISA assay. As expected, RM-PLGA nanocarriers also release insulin in a glucose-responsive manner (FIG. 12C). Further in vivo studies demonstrated that, compared with free insulin+RM-PLGA NPs, insulin-RM-PLGA NPs prolongs the insulin effect to maintain BG levels and reduces the risk of hypoglycemia after injection (FIGS. 12D-G and FIGS. 16A-B).

Figure 10A:
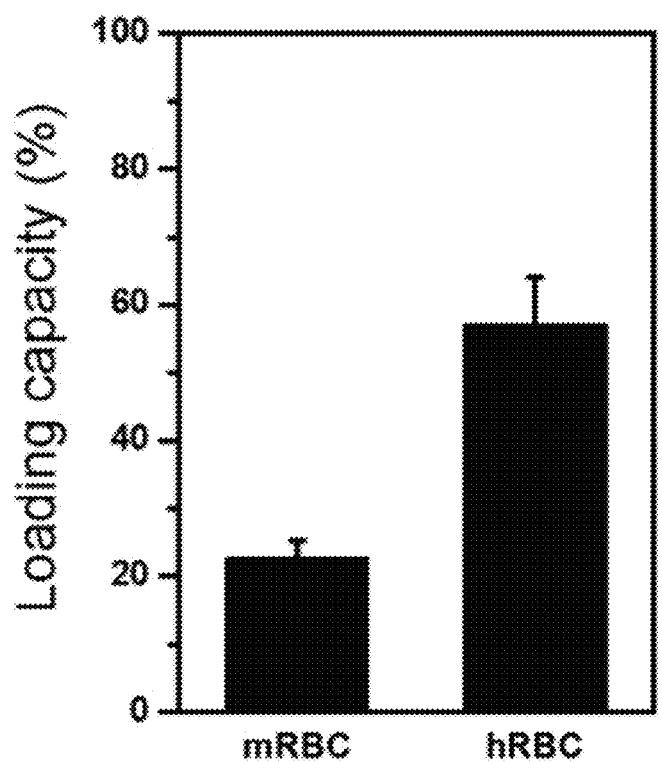
FIG. 10A compares human versus mouse RBCs for glucose-responsive insulin loading and release. $1 \times 10^8$ RBCs were incubated with the 0.5 mg/mL Glu-Insulin in 500 μL PBS overnight. hRBCs show a much higher loading amount of Glu-Insulin than mRBCs. Comparison insulin loading efficiency of mouse and human RBCs. hRBCs showed a much higher loading efficiency of glucose-insulin than mRBCs. Nearly 60% of glucose-insulin was attached to the hRBCs membrane while only approximately 20% of glucose-insulin were detected on mRBCs.
Figure 10B:
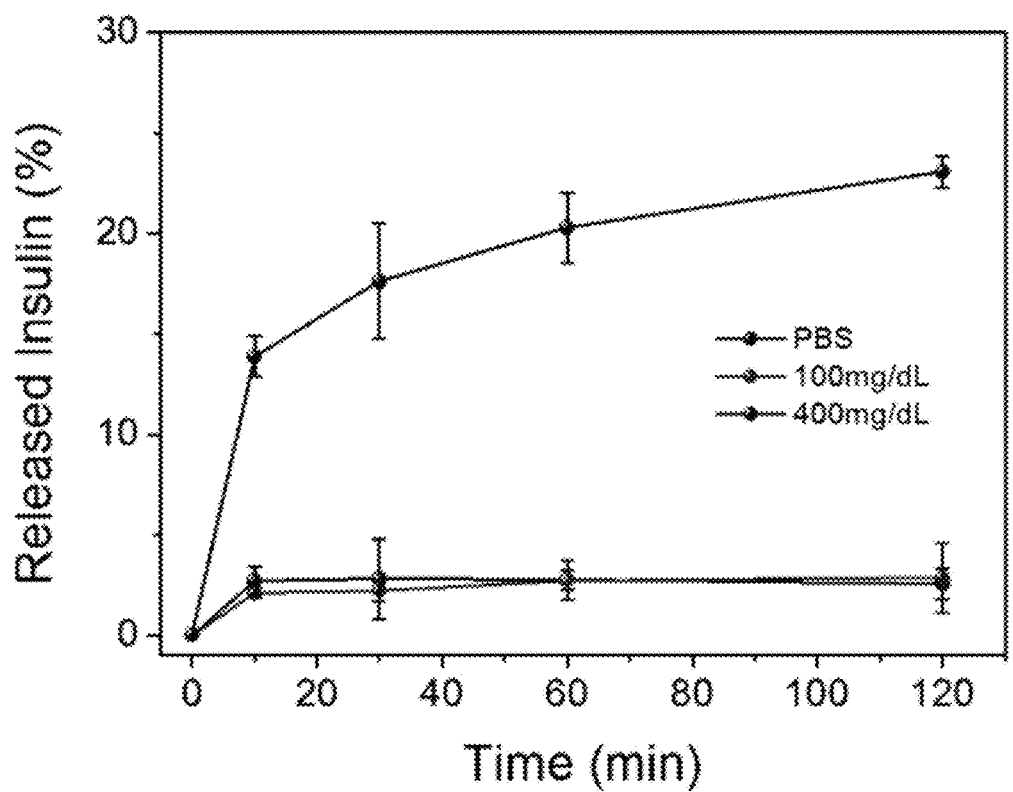
FIG. 10B shows in vitro accumulated insulin release from the hRBCs in several glucose concentrations at 37° C. The insulin release from hRBCs in a glucose-dependent manner was observed.

Example 4. Comparison of Mouse Versus Human RBCs as Glu-Insulin Carriers hRBCs express a higher level of GLUT1 than mRBCs. In fact, GLUT1 accounts for 10% of the total protein mass in the human red cell membrane (Vrhovac, I, et al. Period. Biol. 116, 131-138 (2014)). Therefore, hRBCs may have even better insulin delivery capability than mRBCs. hRBCs and mRBCs were compared in multiple assays to test this hypothesis. First, insulin loading capacity was examined. Nearly 60% of Glu-Insulin was attached to the hRBCs membrane while only 20% of Glu-Insulin was detected on mRBCs (FIG. 10A). Second, glucose-responsive insulin release from hRBCs was validated. (FIG. 10B). More remarkably, insulin release is minimal in the PBS control and in low glucose media, suggesting that the hRBCs with Glu-Insulin are more stable in the normoglycemic environment than insulin-mRBCs (FIG. 5F) and promising for clinical study.

Example 5. Delivery of GLUT1-Glu-Insulin Complex Via Microneedle-Array Patches

Figure 17:
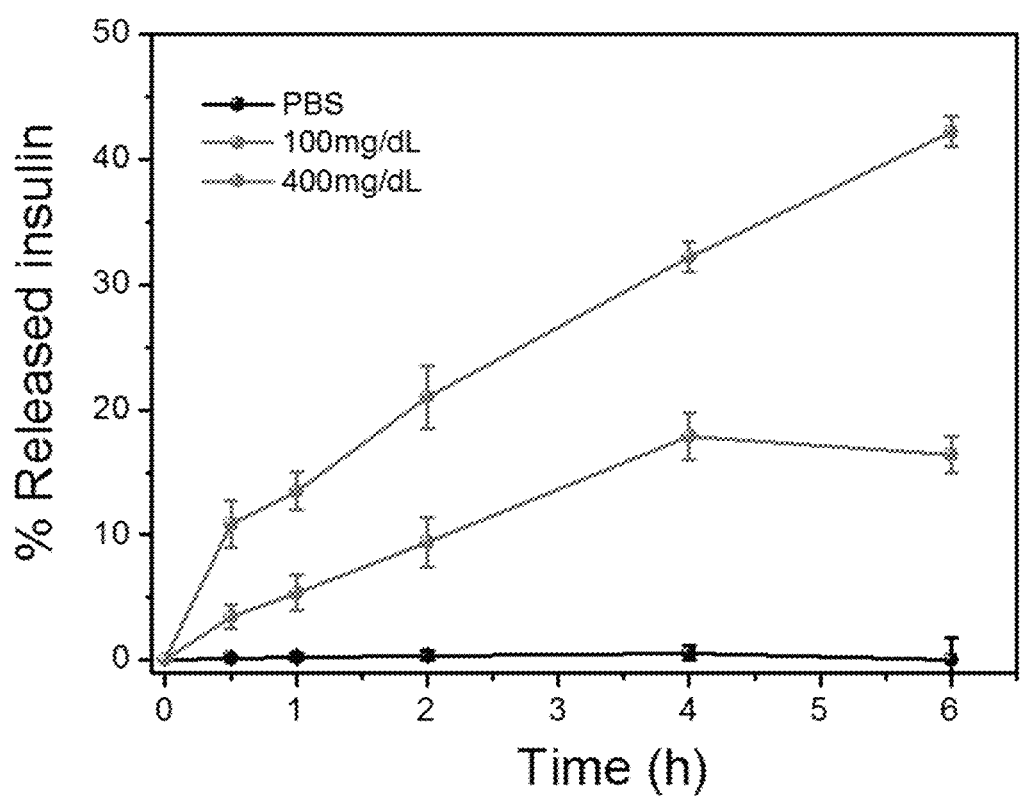
FIG. 17 shows accumulated insulin release from the GLUTs-Insulin conjugates in vitro in several glucose concentrations at 37° C.
Figure 18C:
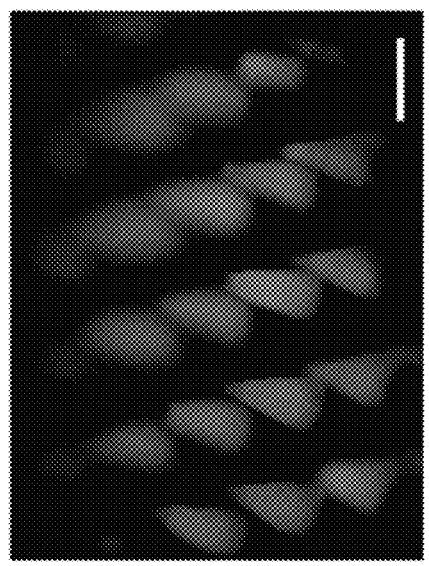
Figure 18B:
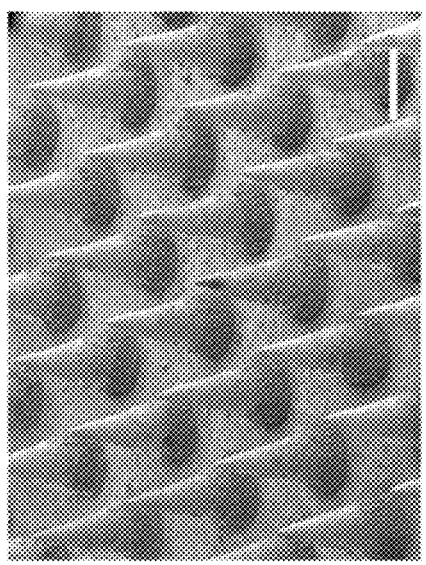
Figure 18A:
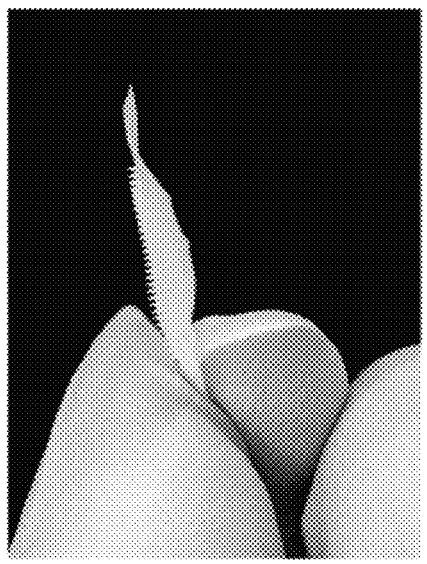
Figure 18F:
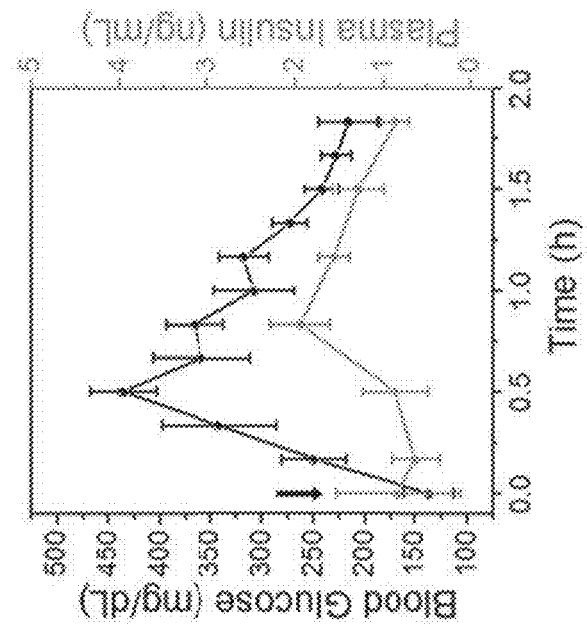
Figure 18E:
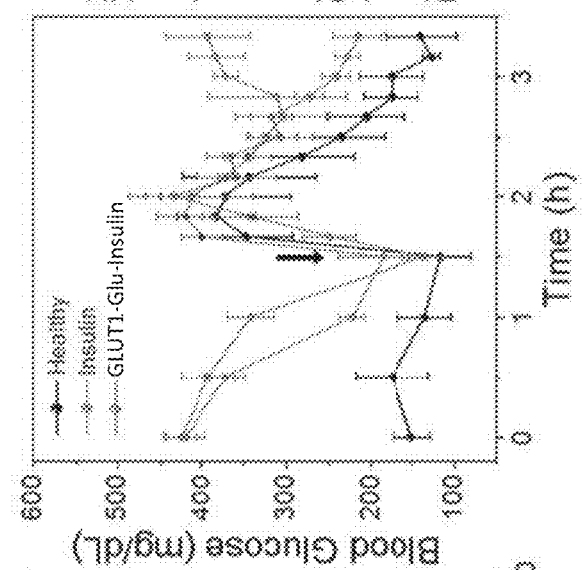
Figure 18D:
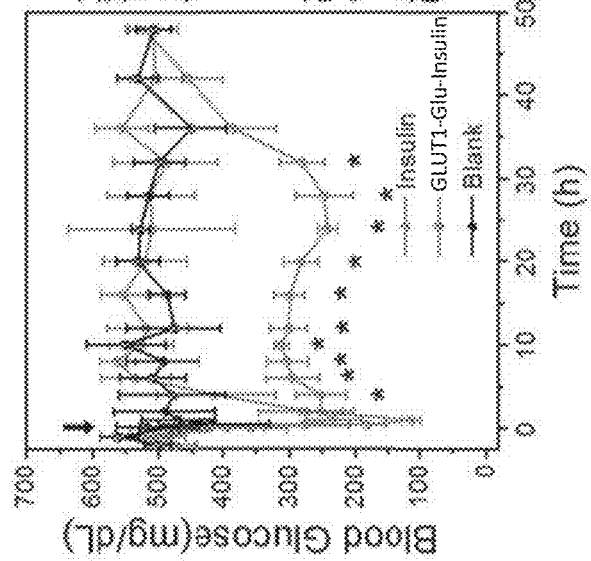
Figure 19:
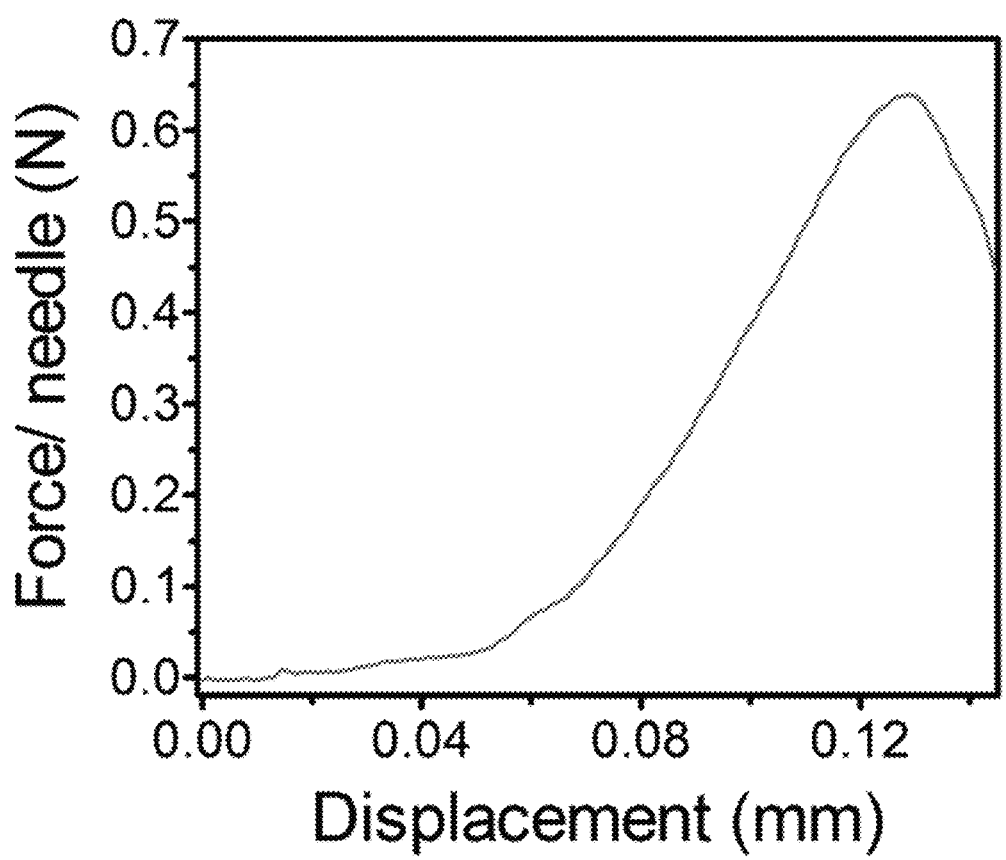
FIG. 19 is a graph showing the mechanical behaviors of GLUT1-Insulin loaded MNs.

GLUT1-Glu-Insulin protein complexes were loaded into microneedle-array (MNs) patches. To test the glucose triggered insulin release, the protein conjugates of GLUT1-Glu-Insulin were incubated in PBS containing different concentrations of glucose as previously mentioned. Released insulin was separated with centrifugal filter device (MWCO=10 kDa) at different time points. As shown in FIG. 17, without glucose, little insulin could be separated. In sharp contrast, when the free glucose were added into the system, glucose concentration and time-dependent insulin release was recorded. Next, the hyaluronic acid (HA)-based MN patch in a 15×15 array with an area of 9×9 mm$^2$ was fabricated using a micromolding approach (Yu J, et al. Proc. Natl. Acad. Sci. U.S.A. 112, 8260-8265 (2015)). Each needle was of conical shape, with 600 µm height and sharp tip tapering to a 5-µm radius of curvature FIG. 18A-C. The mechanical strength of MN was determined as 0.65 N/needle, which was sufficient for skin penetration without breaking FIG. 19.

Figure 20:
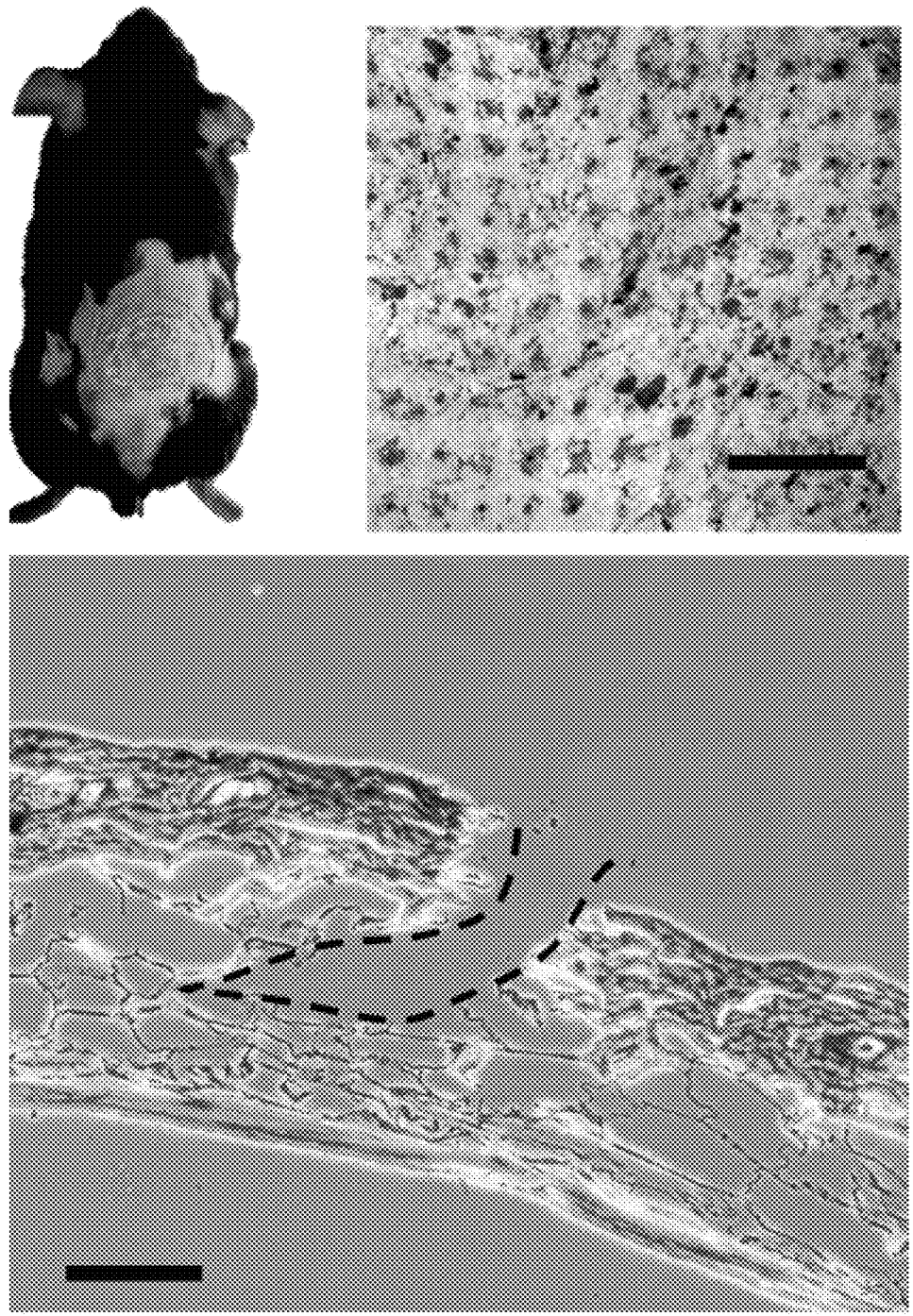
FIG. 20 shows the mouse dorsum and relevant skin transcutaneously treated with an MN-array patch (Top Left), with the image of the trypan blue staining showing MN-array patch penetration of mouse skin (Top Right). (Scale bar: 2 mm) (Bottom) H&E-stained section of mouse skin penetrated by one MN-array patch. (Scale bar: 100 μm).

The smart insulin patch was further investigated in an in vivo study using the STZ mice (FIGS. 18 and 20). Compared with the blank and free insulin loaded MNs, the GLUT1-Glu-Insulin conjugates loaded MNs greatly prolonged the insulin effect to maintain BG levels (FIG. 18D). The glucose tolerance test also suggested that most glucose could be quickly cleared from the blood, which is similar to that recorded associated with the healthy mice (FIG. 18E). Additionally, a peak of plasma insulin levels was observed after IPGTT, indicating that glucose-responsive insulin release profile was achieved in vivo (FIG. 18F).

Figure 21:
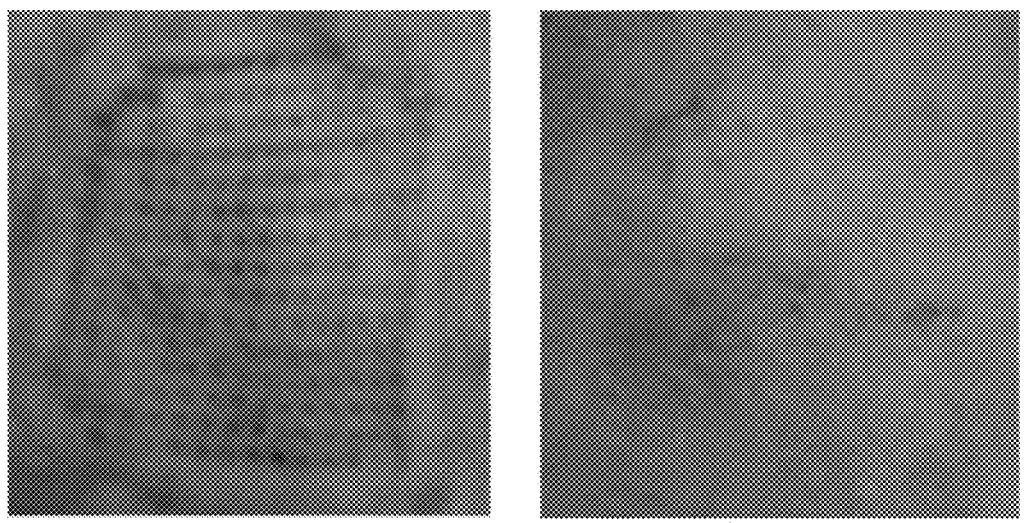
FIG. 21 shows photographs of the skin puncture marks at 5 minutes (left) and 6 hours posttreatment (right).

To further assess the in vivo glucose control capability of MN, the additional administration with MNs was performed. Compared with free insulin-loaded MNs, additional GLUT1-Glu-Insulin MNs administration did not result in the drop of BG to a hypoglycemic level. In contrast, it prolonged the treatment efficiency in response to the elevated BG compared to one dose of MNs administration (FIG. 18G). The study on the healthy mice treated with GLUT1-Glu-Insulin MN patches also evidenced the minimal risk of hypoglycemia induced by GLUT1-Glu-Insulin MN patches (FIG. 18H). The skin treated by the MN patch could rapidly recover within 8 hours after MN removal without any obvious inflammation (FIG. 21). Taken together, the GLUT1-Glu-Insulin MN patches can facilitate a slow and controlled release of an insulin reservoir for regulating BG level in vivo with minimal risk of hypoglycemia.

What is claimed is:

1. An insulin delivery system comprising:
a reservoir;
a composition housed in the reservoir, the composition comprising a glucose binding structure and a glucose-modified insulin molecule reversibly bound to the glucose binding structure,
wherein the glucose-modified insulin molecule comprises an insulin moiety conjugated to at least one glucose moiety by at least one linker molecule.

2. The insulin delivery system of claim 1, wherein the glucose-binding structure releases a portion of the glucose-modified insulin in high glucose conditions.

3. The insulin delivery system of claim 2, wherein high glucose conditions are glucose concentrations greater than or equal to 200 mg/dL.

4. The insulin delivery system of claim 2, wherein the glucose-binding structure binds the glucose modified insulin in low glucose conditions, wherein low glucose conditions are glucose concentrations less than 200 mg/dL.

5. The insulin delivery system of claim 4, wherein the glucose-binding structure is configured to bind the glucose-modified insulin in low glucose conditions for at least 50 days.

6. The insulin delivery system of claim 1, wherein the glucose-modified insulin molecule comprises two or more glucose moieties, wherein each glucose moiety is conjugated to the insulin moiety by a distinct linker molecule.

7. The insulin delivery system of claim 1, wherein the linker molecule is synthetic.

8. The insulin delivery system of claim 7, wherein the linker molecule comprises a maleimide group.

9. The insulin delivery system of claim 7, wherein the linker molecule comprises a polyethylene glycol (PEG) group.

10. The insulin delivery system of claim 1, wherein the insulin delivery system comprises a transdermal patch.

11. The insulin delivery system of claim 1, wherein the insulin delivery system comprises microneedles.

12. The insulin delivery system of claim 1, wherein the glucose-binding structure comprises a GLUT protein.

13. A method of controlling insulin release to a subject using an insulin delivery system, the method comprising:
housing a glucose binding structure and a glucose-modified insulin molecule within a reservoir of the insulin delivery system, the glucose-modified insulin molecule reversibly bound to the glucose binding structure and comprising an insulin moiety conjugated to at least one glucose moiety by at least one linker molecule;

creating a fluidic connection between the reservoir and a blood supply of the subject;

releasing the glucose-modified insulin molecule from the glucose binding structure and into the blood supply as a glucose concentration in the blood supply increases.

14. The method of claim 13, wherein the glucose-modified insulin molecule is released when the glucose concentration in the blood supply is greater than or equal to 200 mg/dL.

15. The method of claim 13, further comprising binding the glucose modified insulin molecule to the glucose binding structure for at least 50 days under low glucose conditions.

16. The method of claim 15, wherein low glucose conditions are glucose concentrations less than 200 mg/dL.

17. The method of claim 13, wherein the reservoir is part of a transdermal patch.

18. The method of claim 13, wherein the reservoir is part of a microneedle-array patch.

19. The method of claim 13, wherein the subject has diabetes.

20. A method of controlling glucose levels in a subject, the method comprising;

administering a therapeutically effective amount of a composition to a subject having diabetes, the composition comprising;

a glucose-modified insulin molecule comprising an insulin moiety conjugated to at least one glucose moiety by at least one linker molecule, and a glucose binding structure, wherein the glucose-modified insulin molecule is reversibly bound to the glucose binding structure, and wherein the glucose-binding structure releases a portion of the glucose-modified insulin in high glucose conditions.

* * * * *